(12) United States Patent
Burger-Kentischer et al.

(10) Patent No.: US 11,104,677 B2
(45) Date of Patent: Aug. 31, 2021

(54) TOLL-LIKE RECEPTOR 9 ANTAGONISTS

(71) Applicants: FRAUNHOFER-GESELLSCHAFT ZUR FÖRDERUNG DER ANGEWANDTEN FORSCHUNG E.V., Munich (DE); YISSUM RESEARCH DEVELOPMENT COMPANY OF THE HEBREW UNIVERSITY OF JERUSALEM, LTD., Jerusalem (IL)

(72) Inventors: Anke Burger-Kentischer, Stuttgart (DE); Angela Mattes, Vaihingen (DE); Maria Zatsepin, Jerusalem (IL); Amriam Goldblum, Jerusalem (IL)

(73) Assignees: FRAUNHOFER-GESELLSCHAFT ZUR FÖRDERUNG DER ANGEWANDTEN FORSCHUNG E.V., Munich (DE); YISSUM RESEARCH DEVELOPMENT COMPANY OF THE HEBREW UNIVERSITY OF JERUSALEM, LTD., Jerusalem (IL)

( * ) Notice: Subject to any disclaimer, the term of this patent is extended or adjusted under 35 U.S.C. 154(b) by 0 days.

(21) Appl. No.: 16/659,198

(22) Filed: Oct. 21, 2019

(65) Prior Publication Data

US 2020/0048252 A1 Feb. 13, 2020

Related U.S. Application Data

(63) Continuation of application No. 15/560,774, filed as application No. PCT/EP2016/056540 on Mar. 24, 2016, now abandoned.

(30) Foreign Application Priority Data

Mar. 24, 2015 (EP) ..................................... 15160521

(51) Int. Cl.
*A61K 31/4155* (2006.01)
*A61K 31/454* (2006.01)
(Continued)

(52) U.S. Cl.
CPC ........ *C07D 471/04* (2013.01); *A61K 31/4155* (2013.01); *A61K 31/454* (2013.01);
(Continued)

(58) Field of Classification Search
CPC ... A61P 37/00; A61K 31/4155; A61K 31/454; A61K 31/496; A61K 31/506; A61K 31/517; A61K 31/5377
See application file for complete search history.

(56) References Cited

U.S. PATENT DOCUMENTS 6,420,391 B1 * 7/2002 Konishi ............... C07D 333/62
514/324
2009/0253134 A1 10/2009 Brunner et al.
2013/0005697 A1 1/2013 Schwede et al.

FOREIGN PATENT DOCUMENTS

DE 102006031483 A1 1/2008
EP 2041172 A1 4/2009
(Continued)

OTHER PUBLICATIONS

Science (1999), vol. 286, 531-537.*
(Continued)

*Primary Examiner* — Rebecca L Anderson
(74) *Attorney, Agent, or Firm* — Harness, Dickey & Pierce, P.L.C.; Stephen T. Olson

(57) ABSTRACT

A method of preventing or treating a disease characterized by an excessive immune response in a subject in need thereof is provided. The method includes administering to the subject a composition including an active component, wherein the active component is a first compound, a second compound, a third compound, a pharmaceutically acceptable salt thereof, a solvate thereof, or a combination thereof, wherein the first, second, and third compounds include:

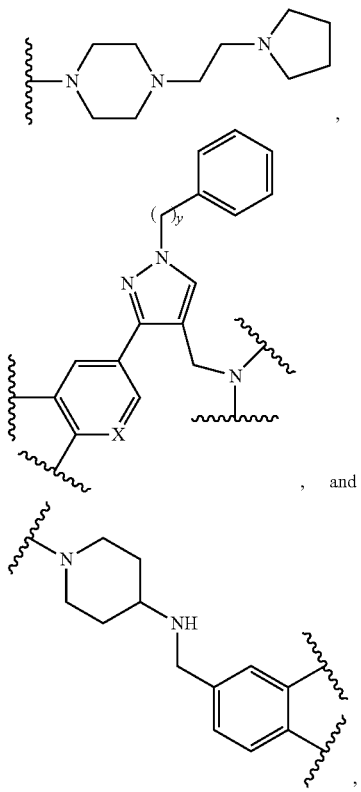

respectively.

16 Claims, 2 Drawing Sheets

Specification includes a Sequence Listing.

(51) Int. Cl.
| | |
|---|---|
| A61K 31/496 | (2006.01) |
| A61K 31/506 | (2006.01) |
| A61K 31/517 | (2006.01) |
| A61K 31/5377 | (2006.01) |
| C07D 471/04 | (2006.01) |
| C07D 413/12 | (2006.01) |
| C07D 239/94 | (2006.01) |
| C07D 405/04 | (2006.01) |
| C07D 295/13 | (2006.01) |
| A61P 37/00 | (2006.01) |
| C07D 231/12 | (2006.01) |
| C07D 401/04 | (2006.01) |
| C07D 401/10 | (2006.01) |
| C07D 403/06 | (2006.01) |
| C07D 403/14 | (2006.01) |
| C07D 407/04 | (2006.01) |
| C07D 407/14 | (2006.01) |
| C07D 413/14 | (2006.01) |
| G01N 33/94 | (2006.01) |

(52) U.S. Cl.
CPC .......... *A61K 31/496* (2013.01); *A61K 31/506* (2013.01); *A61K 31/517* (2013.01); *A61K 31/5377* (2013.01); *A61P 37/00* (2018.01); *C07D 231/12* (2013.01); *C07D 239/94* (2013.01); *C07D 295/13* (2013.01); *C07D 401/04* (2013.01); *C07D 401/10* (2013.01); *C07D 403/06* (2013.01); *C07D 403/14* (2013.01); *C07D 405/04* (2013.01); *C07D 407/04* (2013.01); *C07D 407/14* (2013.01); *C07D 413/12* (2013.01); *C07D 413/14* (2013.01); *G01N 33/94* (2013.01); *G01N 2333/70596* (2013.01); *G01N 2500/04* (2013.01)

(56) References Cited

FOREIGN PATENT DOCUMENTS

| | | | |
|---|---|---|---|
| WO | WO 99/36424 | * | 1/1999 |
| WO | WO 02/49993 | * | 6/2002 |
| WO | WO-2005007672 A2 | | 1/2005 |
| WO | WO-2006078711 A2 | | 7/2006 |
| WO | WO-2008030455 A2 | | 3/2008 |
| WO | WO-2008152471 A1 | | 12/2008 |
| WO | WO-2010036905 A1 | | 4/2010 |
| WO | WO-2011098437 A2 | | 8/2011 |

OTHER PUBLICATIONS

Cancer and Metastasis Reviews (1998), 17(1), 91-106.*
International Search Report and Written Opinion for International Application No. PCT/EP2016/056540, dated Aug. 9, 2016; ISA/EP.
"Ambinter Stock Screening Collection." Database Chemcats, Chemical Abstracts Service, Columbus, OH (Sep. 15, 2014).
Akira, Shizuo and Takeda, Kiyoshi, "Toll-like receptor signalling." Nature Reviews Immunology, vol. 4, No. 7, pp. 499-511 (2004).
Berman, Helen M. et al., "The protein data bank." Nucleic Acids Research, vol. 28, No. 1, pp. 235-242 (2000).
Beutler, Bruce, "Innate immunity: an overview." Molecular Immunology, vol. 40, No. 12, pp. 845-859 (2004).
Botos, Istvan et al., "The structural biology of Toll-like receptors." Structure, Cell Press, vol. 19, No. 4, pp. 447-459 (Apr. 13, 2011).
Burger-Kentischer, Anke et al., "A new cell-based innate immune receptor assay for the examination of receptor activity, ligand specificity, signalling pathways and the detection of pyrogens." Journal of Immunological Methods, vol. 358, No. 1-2, pp. 93-103 (Jun. 30, 2010).
Gaulton, Anna et al., "ChEMBL: a large-scale bioactivity database for drug discovery." Nucleic Acids Research, vol. 40, pp. D1100-D1107 (2012).
Glick, Meir et al., "A stochastic algorithm for global optimization and for best populations: A test case of side chains in proteins." Proceedings of the National Academy of Sciences, vol. 99, No. 2, pp. 703-708 (Jan. 22, 2002).
Hari, Aswin et al., "Toll-like receptors: role in dermatological disease." Mediators of Inflammation, Hindawi Publishing Corporation, vol. 2010, 437246 (Aug. 22, 2010).
Kanzler, Holger et al., "Therapeutic targeting of innate immunity with Toll-like receptor agonists and antagonists." Nature Medicine, vol. 13, No. 5, pp. 552-559 (May 3, 2007).
Nikolova, M. et al., "Pharmacological screening of some mono- and disubstituted piperazine derivatives." Database Caplus, Chemical Abstracts Service, Columbus, OH (Jan. 1, 1974).
Plitas, George et al., "Toll-like receptor 9 inhibition reduces mortality in polymicrobial sepsis." Journal of Experimental Medicine, The Rockefeller University Press, vol. 205, No. 6, pp. 1277-1283 (2008).
Stahura, Florence L. and Bajorath, Jürgen, "New methodologies for ligand-based virtual screening." Current Pharmaceutical Design, vol. 11, No. 9, pp. 1189-1202 (2005).
Stern, Noa and Goldblum, Amiram, "Iterative Stochastic Elimination for Solving Complex Combinatorial Problems in Drug Discovery." Israel Journal of Chemistry, vol. 54, No. 8-9, pp. 1338-1357 (2014).
STN—Chemical Library, "RN 1052090-38-6." Database Registry, Chemical Abstracts Service, Columbus, OH (Sep. 24, 2008).
STN—Chemical Library, "RN 1076236-21-9." Database Registry, Chemical Abstracts Service, Columbus, OH (Nov. 26, 2008).
Wlodawer, Alexander and Vondrasek, Jiri, "Inhibitors of HIV-1 protease: A major success of structure-assisted drug design." Annual Review of Biophysics and Biomolecular Structure, vol. 27, pp. 249-284 (1998).
Zhou, Wei et al., "Toll-like receptor 9 interaction with CpG ODN—An in silico analysis approach." Theoretical Biology and Medical Modelling, vol. 10, 18 (2013).

* cited by examiner

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: phosphorothioated
<220> FEATURE:
<221> NAME/KEY: misc_feature
<222> LOCATION: (3)..(14)
<223> OTHER INFORMATION: phosphodiesters
<220> FEATURE:
<221> NAME/KEY: misc_feature
<222> LOCATION: (15)..(20)
<223> OTHER INFORMATION: phosphorothioated

<400> SEQUENCE: 1
gggggacgat cgtcgggggg           20

TOLL-LIKE RECEPTOR 9 ANTAGONISTS

CROSS-REFERENCE TO RELATED APPLICATIONS

This application is a continuation of U.S. patent application Ser. No. 15/560,774 filed on Sep. 22, 2017, which is a U.S. National Phase Application under 35 U.S.C. 371 of International Application No. PCT/EP2016/056540 filed on Mar. 24, 2016 and published as WO 2016/151085 A1 on Sep. 29, 2016. This application claims priority to European Application No. 15160521.9 filed on Mar. 24, 2015.

BACKGROUND

The present invention relates to a compound or a pharmaceutically acceptable salt thereof or a solvate thereof or a pharmaceutical composition comprising said compound, a process for obtaining or screening for a toll-like receptor 9 (TLR9) antagonist and a toll-like receptor 9 (TLR9) antagonist or a pharmaceutically acceptable salt thereof or a solvate thereof, preferably being obtainable thereby.

Toll-like receptors (TLRs) are part of the Pattern Recognition Receptors (PRRs). TLRs are one of the mechanisms by which our innate immune system senses the invasion of pathogens, due to recognition of specific molecular patterns that are present in microbial components—the pathogen associated microbial patterns (PAMPs) (Beutler, B., Innate immunity: an overview. Mol. Immunol. 2004, 40 (12), 845-859). Human TLR9 is a type I transmembrane protein and is characterized by an extracellular N-terminal ectodomain (ECD) and consists of glycoproteins folded into tandem copies of heavily glycosylated leucine-rich repeats (LRR) and a cytoplasmic TIR domain for the signal transmission. The signaling complex consists of an m-shaped TLR9 dimer (Botos, I.; Segal, D. M.; Davies, D. R., The structural biology of Toll-like receptors. Structure 2011, 19 (4), 447-459). TLR9 activation leads to NF-κB activation and induces positive regulation of the immune response and regulation of cytokine secretion. TLR9 extracellular domain binds the unmethylated CpG short viral or bacterial DNA motifs which are its agonists (Botos, I.; Segal, D. M.; Davies, D. R., The structural biology of Toll-like receptors. Structure 2011, 19 (4), 447-459). The protein is relocalized from endoplasmic reticulum to endosome and lysosome upon stimulation with these agonists (Akira, S.; Takeda, K., Toll-like receptor signalling. Nat. Rev. Immunol. 2004, 4 (7), 499-511).

Although the structure of TLR9 protein has not been elucidated yet, some conclusions regarding the TLR9 binding site may be deduced relying on family homology of the different TLR known structures. All ECDs of reported TLRs structures assume the typical horseshoe-shape with variations in curvature (Botos, I.; Segal, D. M.; Davies, D. R., The structural biology of Toll-like receptors. Structure 2011, 19 (4), 447-459). While in most LRR proteins, ligand binding occurs on the concave surface of the horseshoe, in the known TLR-ligand structures, ligand binding occurs most often on the ascending lateral surface of the TLR-ECD (Botos, I.; Segal, D. M.; Davies, D. R., The structural biology of Toll-like receptors. Structure 2011, 19 (4), 447-459). This surface is the only portion of the molecule that completely lacks N-linked glycan and is free to interact with the ligand and to perform the dimerization of the receptor that leads to the signalling cascade. There is evidence that TLR9 assumes a different conformation than the native one, as it binds CpG DNA. This change could be dependent on the unstructured region (as mentioned above) if it served as a hinge within the horseshoe, thus allowing a large conformational transition to occur for ligand binding. It is reported that in all TLRs, except TLR4, two ECDs cradle a single ligand molecule (Botos, I.; Segal, D. M.; Davies, D. R., The structural biology of Toll-like receptors. Structure 2011, 19 (4), 447-459), hence it is concluded that there is a specific binding site on TLR9 that wasn't mapped in the prior art. The binding agonist leads to conformational changes and to signaling, and antagonists prevent the conformational change and thus cause an inhibition of the TLR9 signal.

TLRs do not only sense microbial invasion but also can be activated by endogenous molecules as well as by low molecular weight synthetic compounds. Given the role of innate immune machinery to provoke inflammation in host, TLRs signaling has been suggested to be involved in the development of many acute and chronic inflammatory processes of allergic and dermatologic diseases (Hari, A.; Flach, T. L.; Shi, Y.; Mydlarski, P. R., Toll-like receptors: role in dermatological disease. Mediators Inflamm. 2010, 2010.). Agonists of the TLRs would be immune system enhancers and have been proposed to be useful in the treatment of cancer and infectious diseases. Antagonists, on the other hand, are thought to have a therapeutic role in suppressing overactive immune responses, as occurs in chronic inflammatory and autoimmune diseases (Hari, A.; Flach, T. L.; Shi, Y.; Mydlarski, P. R., Toll-like receptors: role in dermatological disease. Mediators Inflamm. 2010, 2010; Plitas, G.; Burt, B. M.; Nguyen, H. M.; Bamboat, Z. M.; DeMatteo, R. P., Toll-like receptor 9 inhibition reduces mortality in polymicrobial sepsis. J. Exp. Med. 2008, 205 (6), 1277-83).

TLR9 is expressed within different skin cells types and has been reported to be associated with skin diseases like Atopic dermatitis, Herpes simplex/Varicella zoster, Psoriasis, Lichen Planus, Lupus Erythematosus, Verruca and Molluscum and even as having an exacerbation effect on basal cell carcinoma (Hari, A.; Flach, T. L.; Shi, Y.; Mydlarski, P. R., Toll-like receptors: role in dermatological disease. Mediators Inflamm. 2010, 2010).

TLR9 antagonists are claimed to be useful in treating diseases that are characterized by an unwanted and excessive immune response. Diseases of this type include autoimmune diseases, transplant rejection, and sepsis. Several TLR9 agonists and antagonist are already under preclinical developments (Plitas, G.; Burt, B. M.; Nguyen, H. M.; Bamboat, Z. M.; DeMatteo, R. P., Toll-like receptor 9 inhibition reduces mortality in polymicrobial sepsis. J. Exp. Med. 2008, 205 (6), 1277-83; Kanzler, H.; Barrat, F. J.; Hessel, E. M.; Coffman, R. L., Therapeutic targeting of innate immunity with Toll-like receptor agonists and antagonists. Nat. Med. 2007, 13 (5), 552-559.).

The use of computational approaches for drug discovery and design entered the mainstream of medicinal chemistry as a result of the developments in computer hardware and of the availability of crystal structures of protein targets (Berman, H. M.; Westbrook, J.; Feng, Z.; Gilliland, G.; Bhat, T.; Weissig, H.; Shindyalov, I. N.; Bourne, P. E., The protein data bank. Nucleic Acids Res. 2000, 28 (1), 235-242). Experimental results for protein structures, in particular of protein-ligand complexes, are very useful for computational studies that can accelerate discovery (Wlodawer, A.; Vondrasek, J., Inhibitors of HIV-1 protease: A major success of structure-assisted drug design. Annu. Rev. Biophys. Biomol. Struct. 1998, 27, 249-84). Such structures allow several "structure based" approaches (such as docking and structure based pharmacophore) to be performed in order to discover or design ligands for binding to these proteins. A few Toll Like Receptors structures have been elucidated and are used for predictions and modelling in silico (Zhou, W.; Li, Y.; Pan, X.; Gao, Y.; Li, B.; Qiu, Z.; Liang, L.; Zhou, H.; Yue, J., Toll-like receptor 9 interaction with CpG ODN-An in silico analysis approach. Theoretical Biology and Medical Modelling 2013, 10 (1), 18). However the structure of TLR9 is not known yet from crystallography.

Among "ligand based" methods, Quantitative Structure Property Relations (QSPR) and Classification methods are well known and documented (Stahura, F. L.; Bajorath, J., New methodologies for ligand-based virtual screening. Curr. Pharm. Des. 2005, 11 (9), 1189-1202.; Stahura, F. L.; Bajorath, M., New methodologies for ligand-based virtual screening. Curr. Pharm. Des. 2005, 11 (9), 1189-1202). QSPR focuses on searching relations and correlations between computed properties of molecules and their known biological activities. It is possible in some cases to obtain linear relationships between ligand properties and their known experimental actions, and use the equations (that were formed by employing a small number of molecules) as the basis for predicting the quantitative effects of many others. In classification algorithms in this field, the focus is on discovering the crucial properties that differentiate between active and inactive molecules, or between highly bioactive and weakly bioactive molecules, in general between two groups of molecules. It is usually assumed that classification methods enable to make only binary decisions. However, some classification algorithms produce several classifications in each problem, and those may serve to refine the binary decision by having a "score" (index) for the chance of a molecule to be in one or another class.

There is still a strong need for further TLR9 antagonists which can be applied in methods for treating or preventing diseases with an excessive immune response, as well as a screening method for screening molecule databanks for said potential TLR9 antagonist molecules.

SUMMARY

Thus, the problem underlying the present invention is to provide further TLR9 antagonists and a method for screening a huge variety of different molecules amongst which potential TLR9 antagonists are present. Especially, a process should be provided which significantly reduces the amount of molecules within a search group to a group of target molecules comprising a high percentage of potential TLR9 antagonists.

The problem of the present invention is in particular solved by the subject-matter of the independent claims.

The present invention relates in particular to a process for obtaining a toll-like receptor 9 (TLR9) antagonist, comprising the following steps:
a) providing a group of, preferably virtually represented, search molecules,
b) filtering the group of search molecules, preferably by a software program installed on a computer, based on at least one physico-chemical molecular descriptor as to obtain a first group of target molecules,
c) determining the TLR9 antagonist activity of at least one molecule of the first group of target molecules, preferably in-vitro, preferably in a biological assay, and
d) selecting at least one molecule with a TLR9 antagonist activity as to obtain a toll-like receptor 9 (TLR9) antagonist.

It has been surprisingly found that a filtering based on at least one physico-chemical molecular descriptor, preferably of at least five physico-chemical molecular descriptors, preferably of at least 100 physico-chemical molecular descriptors, results in a high reduction of molecules in the group of search molecules and thereby a group of first target molecules can be obtained, wherein the numbers of molecules is low enough to determine the TLR9 antagonist activity, preferably the IC50 value thereof, based on an in-vitro testing and the probability is relative high that potential TLR9 antagonists are amongst them. Especially, physico-chemical molecular descriptors are used for the specific processes for obtaining and/or screening due to the fact that physico-chemical descriptors can easily be calculated from computer representation of chemical structures of the molecules and do not require elaborated computations.

The present invention relates also to a process for screening for a toll-like receptor 9 (TLR9) antagonist comprising the steps a) and b) of the process for obtaining a toll-like receptor 9 (TLR9) antagonist.

The present invention preferably relates to a process for obtaining or screening for a TLR9 antagonist, wherein in a step a) a group of search molecules is provided.

The term "providing molecules" as stated in process steps (a) and (aa) means that the molecules are provided in a virtual way, i.e. said molecules are present in form of a representation, preferably physico-chemical descriptors' representation, of their chemical structure in a computer or online, preferably in a databank. The molecules are, hence, not provided as real molecules in step (a) and (aa).

The group of search molecules according to step a) is preferably retrieved from, preferably publically available, at least one or more databanks and preferably comprises a high number of molecules, preferably at least 1,000, preferably at least 10,000, preferably at least 100,000, preferably at least 1,000,000, molecules.

In a subsequent process step b), said group of search molecules are filtered based on at least physico-chemical molecular descriptor as to obtain a first group of target molecules. Thus, said group of search molecules are preferably filtered based on a specific value or range of at least one physico-chemical molecular descriptor as to obtain a first group of target molecules.

In context with the present invention the term 'physico-chemical molecular descriptor' is understood as a numerical property of a molecule, which can be calculated from a connection table representation of a molecule. Physico-chemical molecular descriptors describe preferably physical properties, subdivided surface areas, atom counts, bond counts, Kier&Hall Connectivity, Kappa Shape Indices, adjacency and distance matrices, pharmacophore features or partial charges of a molecule. These molecular descriptors are preferably designated as QuaSAR descriptor. Preferably, the physico-chemical molecular descriptors are molecular descriptors of table 6 of the present description. The physico-chemical molecular descriptor is preferably a one dimensional (1D) or two dimensional (2D) descriptor.

Preferably, the group of search molecules are filtered in step b) based on at least 2, preferably at least 5, preferably at least 10, preferably at least 50, preferably at least 100, different physico-chemical molecular descriptors. Preferably, for the filtering in step b) a specific value or a specific range for each physico-chemical molecular descriptor is determined. The value or range for each physico-chemical molecular descriptor is preferably determined in such a way that the MCC score is optimized, preferably is as high as possible. The MCC score is defined as follows:

$$MCC = \frac{(PN) - (P_f N_f)}{\sqrt{(N + N_f)(N + P_f)(P + N_f)(P + P_f)}}$$

wherein P is the proportion of true positives, N is the proportion of true negatives and $P_f$ and $N_f$ are the proportion of false positives and false negatives, respectively, based on the complete numbers of molecules, that is the sum of $P+N+P_f+N_f$. The MCC score is therefore a score which states the discrimination capability of a value or a range of a physico-chemical molecular descriptor between active and inactive or less active molecules or between more active and less active molecules.

Preferably, in step (b) the group of search molecules is filtered firstly by one specific physico-chemical molecular descriptor sorting out said molecules of the group of search molecules which lie outside the specific value or range of the physico-chemical molecular descriptor selected for filtering. Subsequently, the molecules passed through said filter are then filtered by another physico-chemical molecular descriptor which further sorts out those molecules of the group of search molecules lying outside the specifically selected value or range of the physico-chemical molecular descriptor. This procedure applies to all further filters used in step (b). The order of filters is preferably selected in such a way that the discrimination capability between active and inactive molecules or between more active and less active molecules is optimized. Accordingly, the true positive molecules should pass as many filters as desired or possible and the true negative molecules should be filtered out as soon as possible.

The values or ranges of each physico-chemical molecular descriptor contribute to the lowest MCC scores are preferably eliminated as to reduce the number of possible value or range combinations.

In step c), the TLR9 antagonist activity, especially the IC50 value, of at least one molecule of the first group of target molecules is determined. Any molecule which TLR9 antagonist activity, especially the IC50 value, is determined in c) is preferably present as real molecule. Preferably, the TLR9 antagonist activity, preferably the IC50 value, of as many molecules of the first group of target molecules is determined up to at least one TLR9 antagonist is obtained. Preferably, the TLR9 antagonist activity, preferably the IC50 value, of all molecules of the first group of target molecules is determined.

In context with the present invention, the 'IC50 value' is the half maximum inhibitory concentration which is a measure of the effectiveness of a substance inhibiting the function of the TLR9. The IC50 value can be determined by a functional antagonist assay or a competition binding assay. Preferably, the IC50 value is determined by the cell-based reporter assay in section 3, below, of the examples.

In step d), at least one toll-like receptor 9 antagonist is obtained. Said at least one TLR9 antagonist has preferably an IC50 value of at most 500 µmol, preferably at most 100 µmol, preferably at most 50 µmol, preferably at most 1 µmol, preferably at most 500 nmol, preferably at most 250 nmol.

Preferably, the first group of target molecules is filtered based on at least one molecular property which can be used for defining, preferably known, TLR9 antagonists or having a direct influence on the, preferably competitive, binding behavior of molecules to TLR9. Said filtering is inter alia termed herein as "applicability domain" filtering.

The present invention preferably relates to a process, wherein the first group of target molecules is further filtered based on at least one molecule property selected from the group of molecular weight, log P (logarithm of partition coefficient), number of hydrogen bond donors and number of hydrogen bond acceptors, as to obtain a second group of target molecules and the TLR9 antagonist activity of at least one molecule of the second group of target molecules is determined in step c).

Preferably, at least two, preferably at least three, preferably all four molecule properties selected from said group are used for the filtering of the first group of target molecules. Preferably, a value or a range is determined for each molecule property. The value or ranges of the at least one molecule property is determined in such that an optimized MCC score, preferably a MCC score as high as possible, is obtained.

Preferably, in said step the first group of target molecules is filtered firstly by one specific molecule property sorting out said molecules of the group of target molecules which lie outside the specific value or range of the molecule property selected for filtering. Subsequently, the molecules passed through said filter are then filtered by another molecule property which further sorts out those molecules of the group of target molecules lying outside the specifically selected value or range of the molecule property. This procedure applies to all further filters used in said step. The order of filters is preferably selected in such a way that the discrimination capability between (i) active and (ii) inactive and/or less active molecules is optimized. Accordingly, the true positive molecules should pass as many filters as desired or possible and the true negative molecules should be filtered out as soon as possible.

The present invention preferably relates to a process, wherein the second group of target molecules is filtered based on their solubility as to obtain a third group of target molecules and the TLR9 antagonist activity of at least one molecule of the third group of target molecules is determined in step c).

Preferably, the solubility, preferably the intrinsic solubility, of the molecules of the second group of target molecules, preferably in form of their logarithm (log S), is determined in silico, that is based on at least one, preferably at least three, preferably at least five, preferably exactly five different software programs. The software program is preferably selected from the VCCLAB program, the LMMD program, the SciFinder program, the MOE program and the Enamine program. Preferably, the average of the solubilities calculated by the different software programs and its standard deviation is calculated. Preferably, the averaged solubility value is used for filtering.

The present invention preferably relates to a process, wherein the third group of target molecules has a log S (logarithm of solubility) of −8.0 or higher. Preferably, the third group of target molecules has a log S of, −7.0 or higher, preferably, −6.0 or higher, preferably −5.0 or higher, preferably −4.0 or higher, preferably of −3.0 or higher, preferably from −6.0 to −2.0.

Preferably, the molecules of the second group of target molecules are separated into molecules having a low solubility and a high solubility. Preferably, they are separated by the logarithm of solubility, namely having either a log S of −8.0 or higher or a log S of lower than −8.0. Molecules with a log S of −8.0 or higher are selected as molecules of the third group of target molecules.

Using in-silico solubility models is advantageous over measurements of aqueous solubility, especially the intrinsic solubility, based on chemical experiments. The in silico models for evaluation of the solubility have a high quality and reliability, especially if two or more solubilities calculated by different solubility software programs are averaged.

Furthermore, by further filtering the first group of target molecules by at least one molecule property which is designated to be crucial for the binding activity of a molecule to the TLR9 and/or by the further filtering based on the solubility of the target molecules to be obtained further increases the reduction of the group of target molecules obtained.

Preferably, all three different filtering steps, namely the filtering based on at least one physico-chemical molecular descriptor, on at least one molecule property and on the solubility is performed, preferably in said order.

Preferably, the physico-chemical molecular descriptor based filters used in step (b) are different from the filters based on at least one molecule property used for filtering the first group of target molecules.

The present invention preferably relates to a process, wherein the filtering in step b) is performed by using a model system.

The present invention preferably relates to a process, wherein the model system is prepared by:
(aa) providing (i) a group of known active molecules known to be TLR9 antagonists and (ii) a group of inactive and/or less active molecules,
(bb) calculating physico-chemical molecular descriptors of the molecules of the group of known active molecules and of the group of inactive and/or less active molecules and
(cc) selecting at least one physico-chemical molecular descriptor of the calculated physico-chemical molecular descriptors for filtering the group of search molecules.

Under the term 'active molecules' molecules are understood which are known to be TLR9 antagonists, either by reports of the prior art or by determination of the TLR9 antagonist activity, preferably the IC50 value, in accordance with the present invention.

In context with the present invention, 'inactive or less active molecules' are understood to be molecules having no TLR9 antagonist activity or a TLR9 antagonist activity with an IC50 value of 3 mmol or more, preferably 1,000 µmol or more, preferably 500 µmol or more, preferably 3 µmol or more.

In a preferred embodiment of the present invention, the filtering of the group of search molecules in step b) is performed by a model system which has been trained to filter potential TLR9 antagonist molecules from molecules having no TLR9 antagonist activity. It is very clear that the filtering of a group of search molecules also preferably results in a sort out of molecules which are TLR9 receptor antagonists. However, the main aim of the present invention is to reduce the number of molecules in a group of target molecules and improving the probability of the presence of potential TLR9 antagonist molecules within the group of target molecules.

The model system is prepared, preferably trained, by providing, firstly, in step (aa) a group of active molecules known to be TLR9 antagonists and a group of inactive and/or less active molecules. The group of known active molecules comprises molecules with an IC50 value of at most 1,000 nmol, preferably at most 500 nmol, preferably at most 250 mmol. The group of inactive and/or less active molecules comprises a large number of molecules comprising both some TLR9 antagonists and a huge amount of molecules being no TLR9 antagonists or known least active antagonists. Preferably, the group of inactive or less active molecules consists of molecules having no binding activity to TLR9 or low binding affinity to TLR9. The group of inactive and/or less active molecules comprises preferably at least 95%, preferably at least 98%, preferably at least 99%, preferably at least 99.9%, preferably 100%, molecules having no binding activity to the TLR9.

Alternatively, the group of inactive and/or less active molecules preferably consists of molecules with an IC50 value of 3 µmol or more, preferably 500 µmol or more, preferably 1,000 µmol or more, preferably 3 mmol or more.

Preferably, in step (bb) physico-chemical molecular descriptors, preferably the physico-chemical molecular descriptor of table 6, are calculated for each molecule of the group of known active molecules and of the group of inactive molecules and/or of the less active molecules. Subsequently, in step (cc) at least one, preferably at least two, preferably at least five, preferably at least 50, preferably at least 100, different physico-chemical molecular descriptors of the in step (bb) calculated physico-chemical molecular descriptors are selected for filtering the group of search molecules provided in step (a). Preferably, a value or a range of each physico-chemical molecular descriptor is determined, preferably software based. Preferably, the value and the range of each physico-chemical molecular descriptor is determined in such that the MCC score is optimized, preferably as high as possible, for said specific physico-chemical molecular descriptor.

Preferably, the selection of at least one specific physico-chemical molecular descriptor of the in step (bb) calculated physico-chemical molecular descriptors and their value or their range is based on an iterative stochastic elimination algorithm. Preferably, said specific selection is based on a specific software-based algorithm within a lot of different cycles of filtering and determination of specific physico-chemical molecular descriptor(s). The adjusting and selecting of the specific physico-chemical molecular descriptor(s) and their values or ranges is performed as to result in the most promising ones for distinguishing between active and inactive molecules or between more active and less active molecules.

The present invention preferably relates to a process, wherein prior to step (b) and/or (bb) molecules with a molecular weight of 150 g/mol or less, preferably 100 g/mol or less, and/or of 1500 g/mol or more, preferably 1300 g/mol or more, are removed from at least one of the groups of known active molecules, of inactive and/or less active molecules and of search molecules. Said removal is performed preferably by the program 'WASH' of the MOE software. Preferably, prior to step (b) and/or (bb) molecules with a molecular weight 150 g/mol or less, preferably 100 g/mol or less, and/or of 1500 g/mol or more, preferably 1300 g/mol or more are removed from all groups of known active molecules, of inactive and/or less active molecules and of search molecules. By removing said molecules, significance of the model system and the discrimination capability of each physico-chemical molecular descriptor used is improved.

Preferably, steps (b) and/or (bb) anions with a molecular weight of 150 g/mol or less, preferably 100 g/mol or less, and/or of 1,500 g/mol or more, preferably 1,300 g/mol are removed from at least one of the groups of known active molecules, inactive and/or less active molecules and search molecules. Preferably, steps (b) and/or (bb) anions with a molecular weight of 150 g/mol or less, preferably 100 g/mol or less, and/or of 1,500 g/mol or more, preferably 1,300 g/mol are removed from all groups of known active molecules, inactive or less active molecules and search molecules.

Preferably, the group of inactive and/or less active molecules consists of molecules being similar to the known active molecules and having thereof at least one of molecular weight of 1500 to 150 g/mol, preferably 1300 to 300 g/mol, a calculated log P (logarithm of partition coefficient) of less than 5, a number of hydrogen bond donors of 1 to 5 and a number of hydrogen bond acceptors of 1 to 5.

The present invention preferably relates to a process, wherein the process is free of a Tanimoto filtering.

Alternatively, the group of known active molecules is preferably filtered by Tanimoto's similarity method. Preferably, the Tanimoto coefficient $T_c$ of each pair of two molecules comprised in the group of active molecules is determined. The Tanimoto coefficient is defined as follows:

$$T_c = \frac{c}{a+b-c}$$

wherein a and b are the bit sets of molecule A and molecule B and c is the number of bits present in both molecules.

By performing the Tanimoto's similarity method, active molecules are preferably kept in the group of active molecules if their Tanimoto coefficient is 85% or lower, preferably 75% or lower, preferably 70% or lower to any other molecules in the group of active molecules. If the Tanimoto coefficient is higher than 85%, preferably 75%, preferably 70% of two different molecules, the molecule either with the higher or lower, preferably lower, IC value is preferably kept in the group.

The present invention preferably relates to a process, wherein prior to step (bb) molecules from the group of inactive or less active molecules are removed, which molecular weight, calculated log P (logarithm of partition coefficient), number of hydrogen bond donors or number of hydrogen bond acceptors deviates more than plus or minus two standard deviations from the average value of all molecules of the group of active molecules.

Preferably, prior to steps (b) and/or (bb), molecules are removed from the group of inactive or less active molecules and/or a group of search molecules, which molecular weight, calculated log P (logarithm of partition coefficient), number of hydrogen-bond donors and number of hydrogen-bond acceptors deviate more than +/−two standard deviations from the average value of all active molecules in the group of active molecules.

In a preferred embodiment a process for obtaining or screening for a toll-like receptor 9 (TLR9) antagonist, is provided which comprises the following steps:

(aa) providing (i) a group of known active molecules known to be TLR9 antagonists, (ii) a group of inactive and/or less active molecules and (iii) a group of search molecules, (bb) calculating physico-chemical molecular descriptors of the molecules of the group of known active molecules and of the group of inactive and/or less active molecules, (cc) selecting at least one distinguishing physico-chemical molecular descriptor of the calculated physico-chemical molecule descriptors, (dd) determining a value or a range for the at least one distinguishing physico-chemical molecular descriptor for filtering the group of search molecules, preferably based on the MCC score, (ee) filtering the group of search molecules based on the value or the range for the at least one distinguishing physico-chemical molecular descriptor as to obtain a first group of target molecules, (ff) filtering the first group of target molecules based on at least one molecule property selected from the group of molecular weight, log P (logarithm of partition coefficient), number of hydrogen bond donors and number of hydrogen bond acceptors, as to obtain a second group of target molecules, (gg) filtering the second group of target molecules based on their solubility as to obtain a third group of target molecules, (hh) determining the TLR9 antagonist activity of at least one molecule of the third group of target molecules and (jj) selecting at least one molecule with a TLR9 antagonist activity determined in step (c) as to obtain a toll-like receptor 9 (TLR9) antagonist.

In a preferred embodiment a process for screening for a toll-like receptor 9 (TLR9) antagonist, comprises the steps (aa) to (gg).

Preferably, physico-chemical molecular descriptors are eliminated, preferably in step (cc), which are highly correlated descriptors or are descriptors with low standard deviations within the group of active molecules and/or the group of inactive and/or less active molecules. Preferably, the Linear Correlation Matrix produced by KNIME software is used for said elimination.

Preferably, the process according to the present invention is based on a five-fold type study. Accordingly, five initial ISE model systems are preferably created from a five-fold data partitions while the final ISE model is constructed from the combination of all of those five models together.

Each molecule of the group of search molecules can be assigned to a specific score, also called ISE value or ISE index. Said index ranges from −1 to +1. A molecule having an index of −1 does not pass any filters used during the filtering process. A molecule passing all filters has the index of +1. A molecule with the index of +1 has the highest probability to be an active molecule and a molecule with the index of −1 has the highest probability to be an inactive or less active molecule. Thus, by using the model system, a specific ISE index can be assigned to each molecule. Said indices can be illustrated in a table (see for instance FIGS. 1 and 2) allowing the selection of a group of targeting molecules having a specific ICE index or higher, that is a specific probability to be an active molecule and determine their TLR9 antagonist activity, especially their IC50 values, in vitro based on a receptor assay.

Preferably, molecules are selected as target molecules in each filtering step having an ISE index of at least 0.1, preferably at least 0.2, preferably at least 0.3, preferably a least 0.4, preferably at least 0.5.

Preferably, the toll-like receptor 9 (TLR9) antagonist obtained according to the present invention are used as further active molecules in the group of know active molecules.

The present invention also relates to a compound or a pharmaceutically acceptable salt thereof or a solvate thereof or a pharmaceutical composition comprising the compound for use in a method for treatment, preferably of the human or animal body, wherein the compound is selected from the group of compounds:

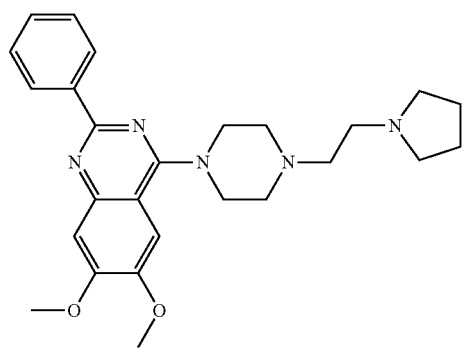
1
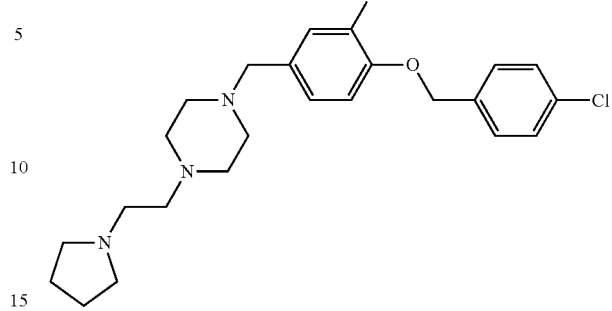
5
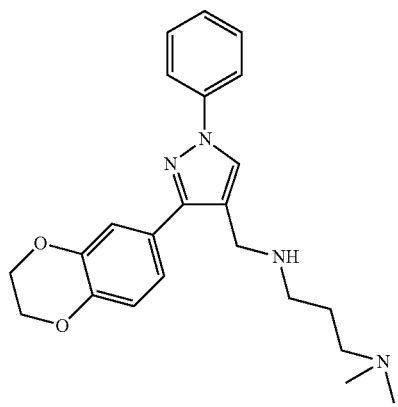
2
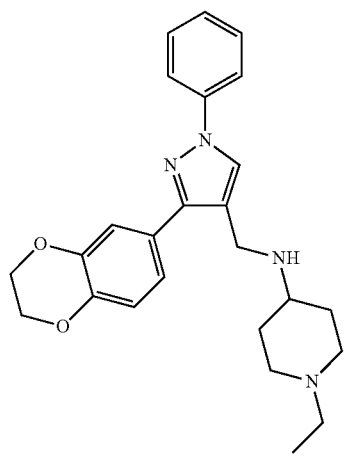
6
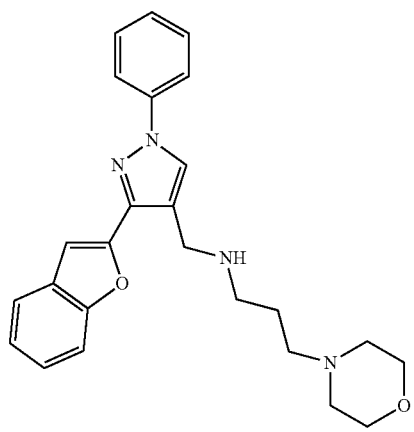
3
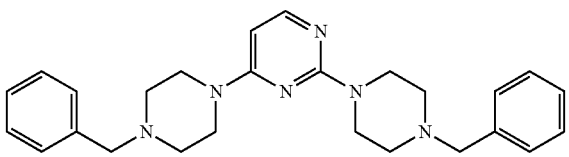
7
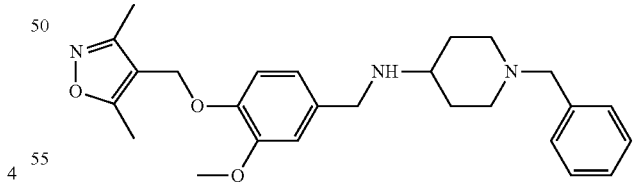
8
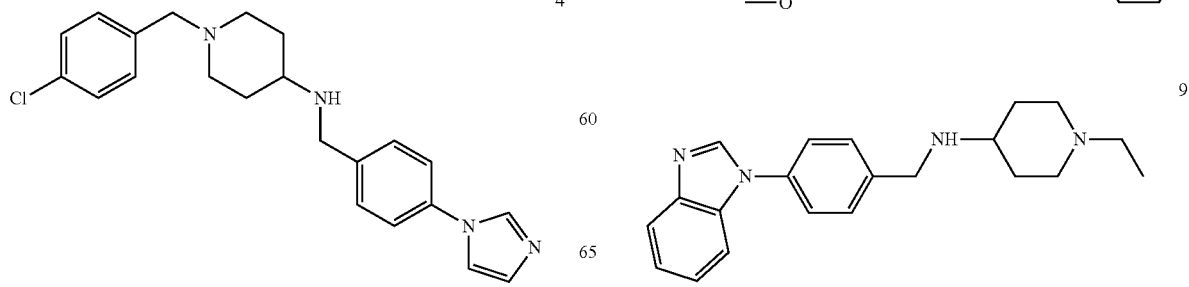
4
9

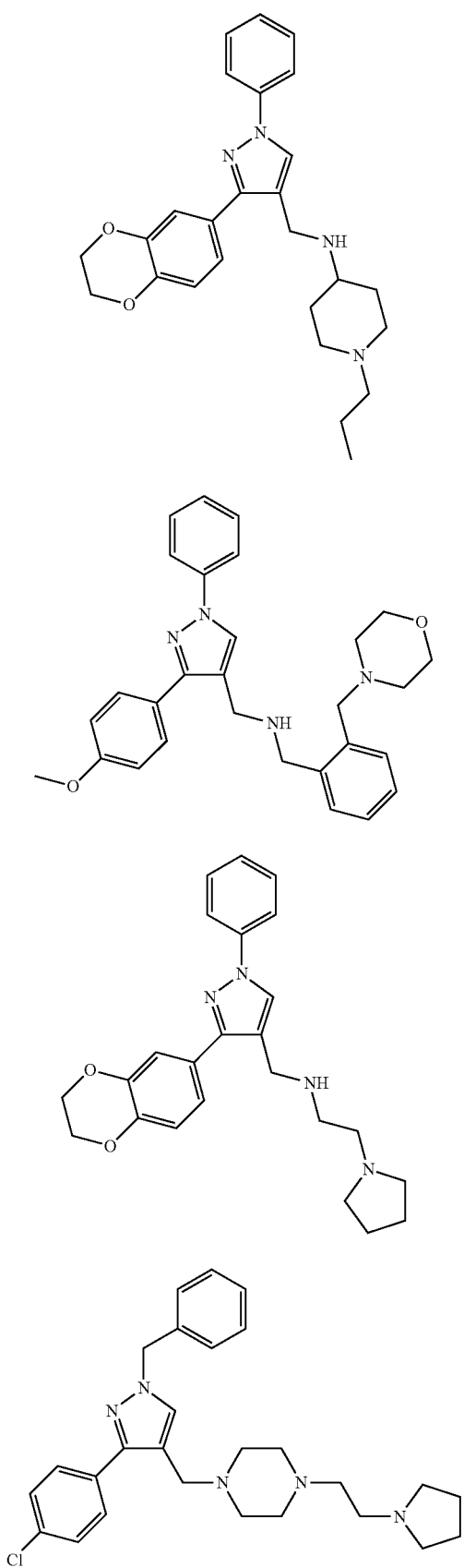
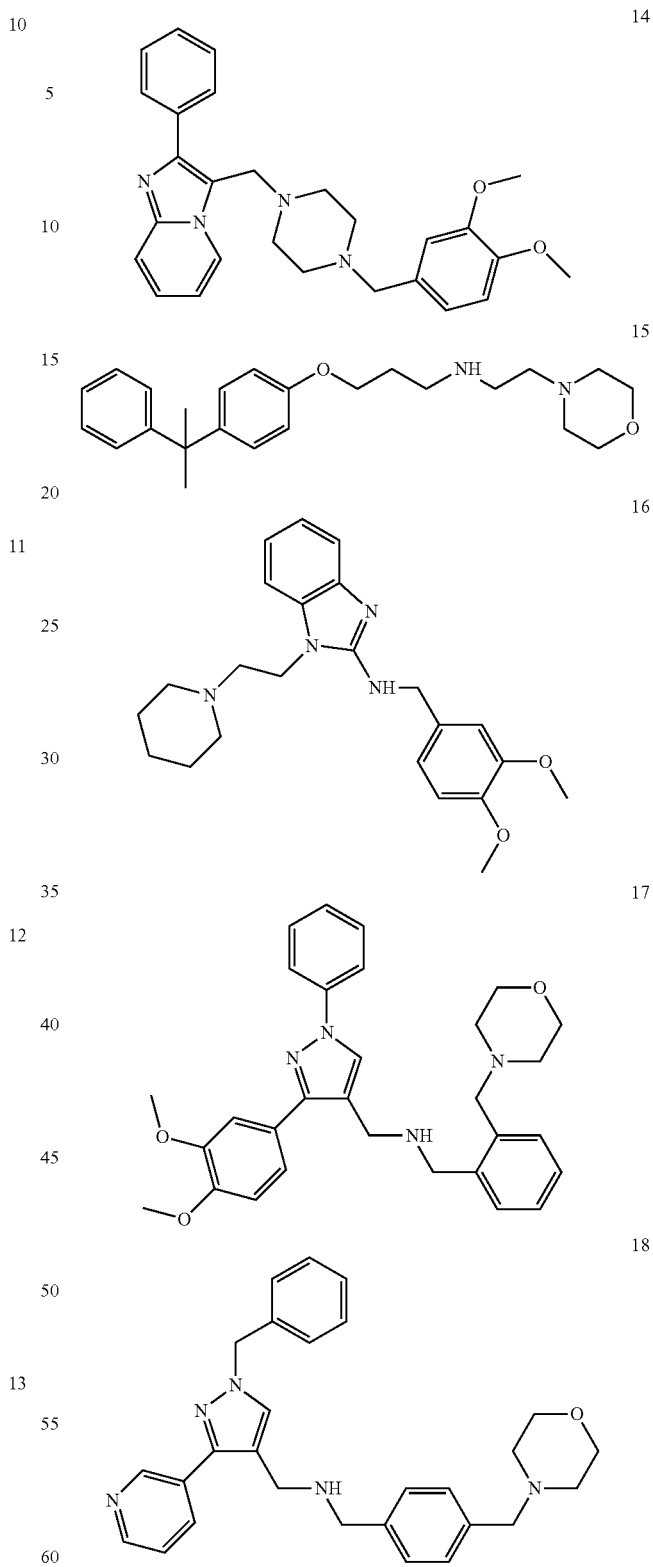
The present invention preferably relates to a compound or a pharmaceutically acceptable salt thereof or a solvate thereof or a pharmaceutical composition comprising the compound for use in a method for treatment, preferably of the human or animal body, wherein the compound is

1

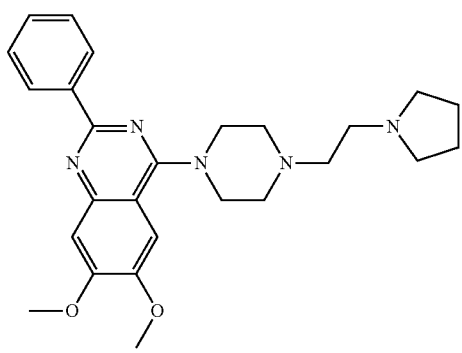

The present invention preferably relates to a compound or a pharmaceutically acceptable salt thereof or a solvate thereof or a pharmaceutical composition comprising the compound for use in a method for treatment, preferably of the human or animal body, wherein the compound is

2

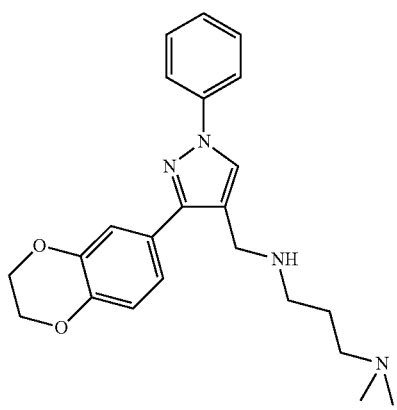

The present invention preferably relates to a compound or a pharmaceutically acceptable salt thereof or a solvate thereof or a pharmaceutical composition comprising the compound for use in a method for treatment, preferably of the human or animal body, wherein the compound is

3

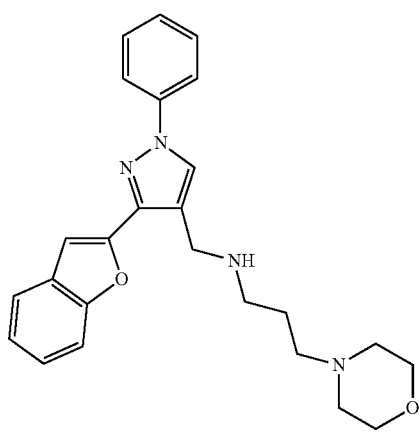

The present invention preferably relates to a compound or a pharmaceutically acceptable salt thereof or a solvate thereof or a pharmaceutical composition comprising the compound for use in a method for treatment, preferably of the human or animal body, wherein the compound is

4

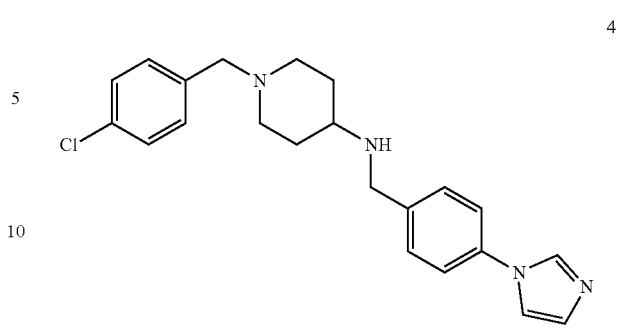

The present invention preferably relates to a compound or a pharmaceutically acceptable salt thereof or a solvate thereof or a pharmaceutical composition comprising the compound for use in a method for treatment, preferably of the human or animal body, wherein the compound is

5

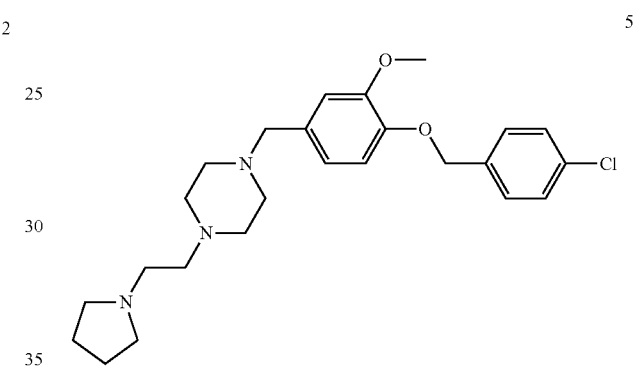

The present invention preferably relates to a compound or a pharmaceutically acceptable salt thereof or a solvate thereof or a pharmaceutical composition comprising the compound for use in a method for treatment, preferably of the human or animal body, wherein the compound is

6

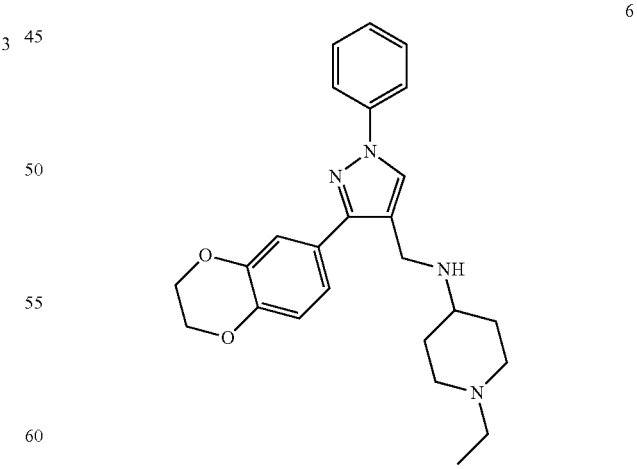

The present invention preferably relates to a compound or a pharmaceutically acceptable salt thereof or a solvate thereof or a pharmaceutical composition comprising the compound for use in a method for treatment, preferably of the human or animal body, wherein the compound is

7

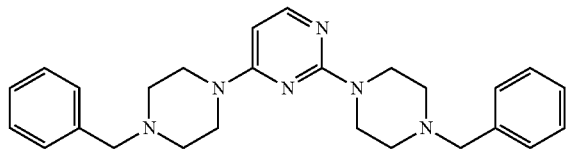

The present invention preferably relates to a compound or a pharmaceutically acceptable salt thereof or a solvate thereof or a pharmaceutical composition comprising the compound for use in a method for treatment, preferably of the human or animal body, wherein the compound is

8

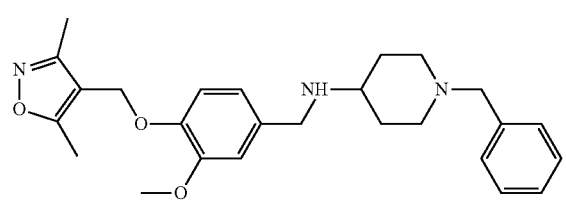

The present invention preferably relates to a compound or a pharmaceutically acceptable salt thereof or a solvate thereof or a pharmaceutical composition comprising the compound for use in a method for treatment, preferably of the human or animal body, wherein the compound is

9

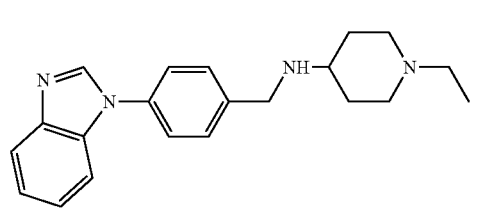

The present invention preferably relates to a compound or a pharmaceutically acceptable salt thereof or a solvate thereof or a pharmaceutical composition comprising the compound for use in a method for treatment, preferably of the human or animal body, wherein the compound is

10

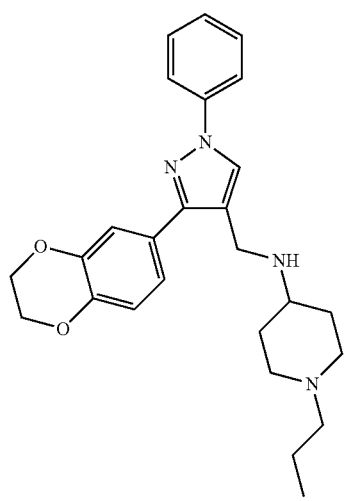

The present invention preferably relates to a compound or a pharmaceutically acceptable salt thereof or a solvate thereof or a pharmaceutical composition comprising the compound for use in a method for treatment, preferably of the human or animal body, wherein the compound is

11

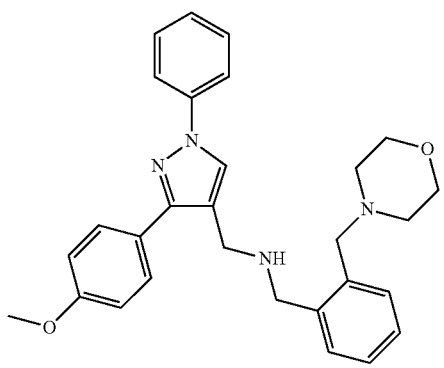

The present invention preferably relates to a compound or a pharmaceutically acceptable salt thereof or a solvate thereof or a pharmaceutical composition comprising the compound for use in a method for treatment, preferably of the human or animal body, wherein the compound is

12

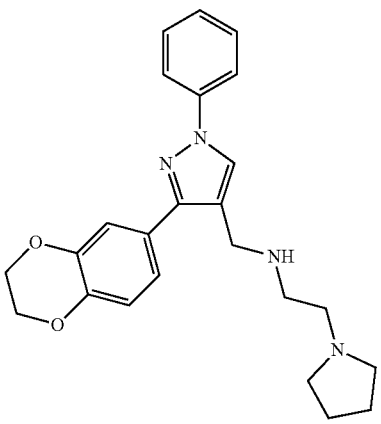

The present invention preferably relates to a compound or a pharmaceutically acceptable salt thereof or a solvate thereof or a pharmaceutical composition comprising the compound for use in a method for treatment, preferably of the human or animal body, wherein the compound is

13

The present invention preferably relates to a compound or a pharmaceutically acceptable salt thereof or a solvate thereof or a pharmaceutical composition comprising the compound for use in a method for treatment, preferably of the human or animal body, wherein the compound is

14

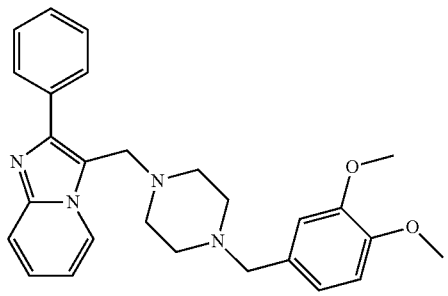

The present invention preferably relates to a compound or a pharmaceutically acceptable salt thereof or a solvate thereof or a pharmaceutical composition comprising the compound for use in a method for treatment, preferably of the human or animal body, wherein the compound is

15

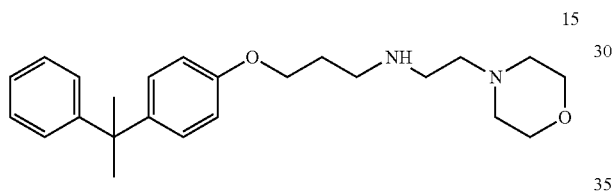

The present invention preferably relates to a compound or a pharmaceutically acceptable salt thereof or a solvate thereof or a pharmaceutical composition comprising the compound for use in a method for treatment, preferably of the human or animal body, wherein the compound is

16

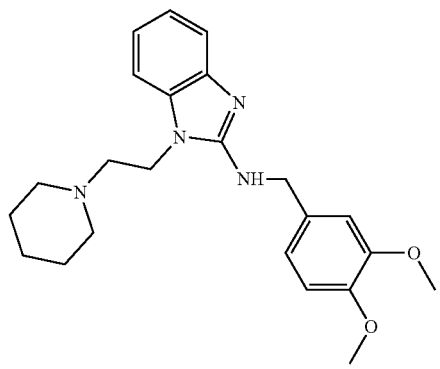

The present invention preferably relates to a compound or a pharmaceutically acceptable salt thereof or a solvate thereof or a pharmaceutical composition comprising the compound for use in a method for treatment, preferably of the human or animal body, wherein the compound is

17

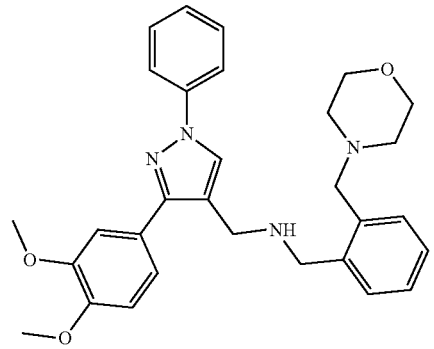

The present invention preferably relates to a compound or a pharmaceutically acceptable salt thereof or a solvate thereof or a pharmaceutical composition comprising the compound for use in a method for treatment, preferably of the human or animal body, wherein the compound is

18

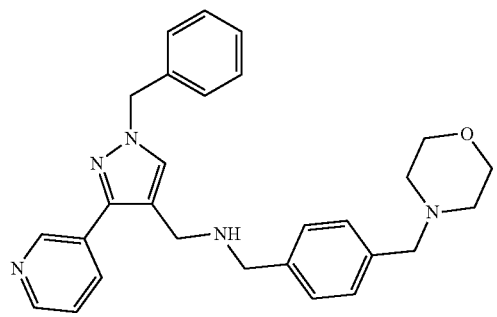

The present invention preferably relates to a compound or a pharmaceutically acceptable salt thereof or a solvate thereof or a pharmaceutical composition comprising the compound for use in a method for treatment, preferably of the human or animal body, wherein the compound can be represented by the structure of

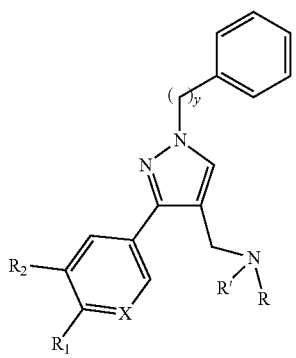

wherein y is 0 or 1 and X is CH or N and which can be preferably designated as 1-aryl-3-phenyl-1H-pyrazol-4-yl-methylamine or 1-aryl-3-pyridyl-1H-pyrazol-4-ylmethyl-amine and is selected from the group of compounds:

21
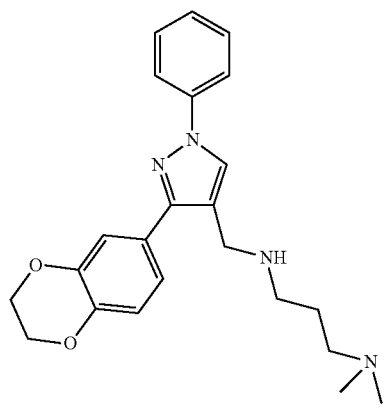
2
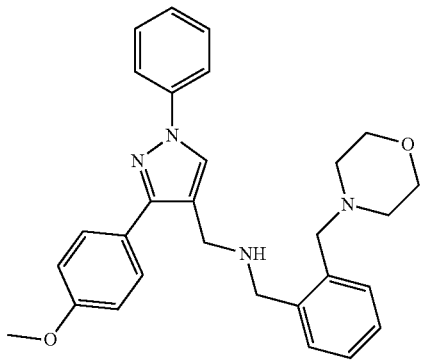
11
6
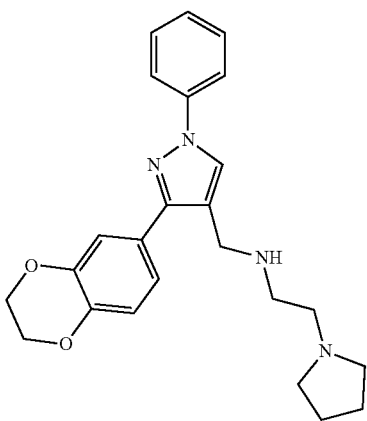
12
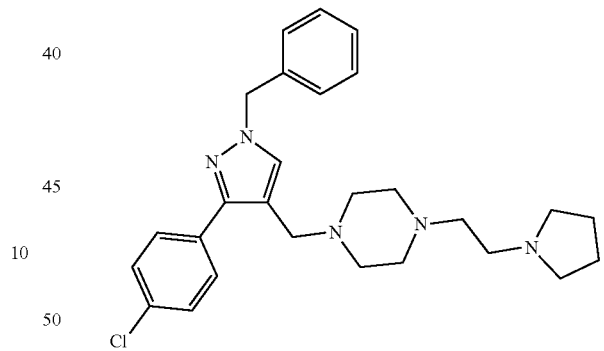
13
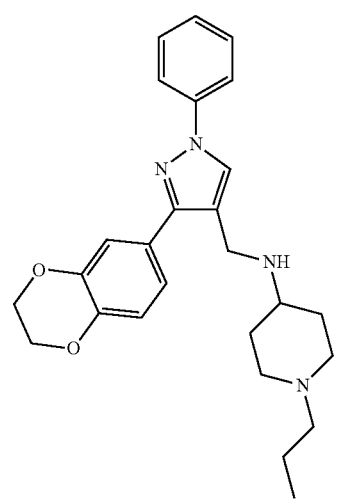
10
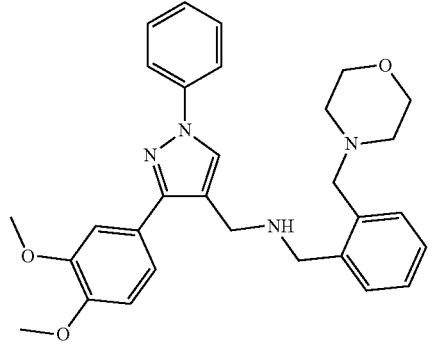
17

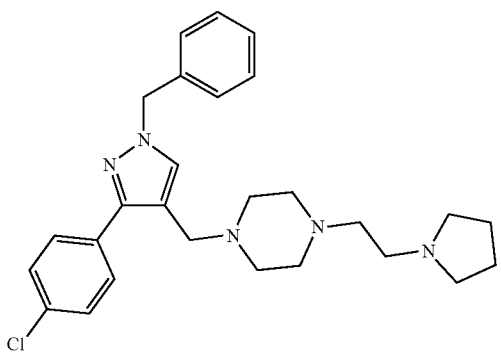

18

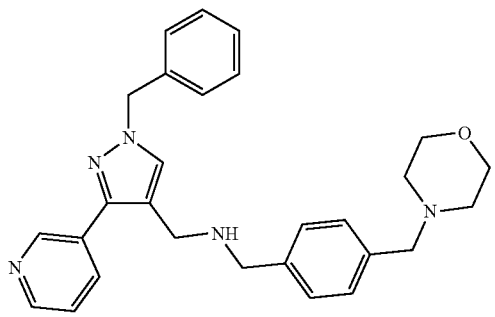

13

The present invention preferably relates to a compound or a pharmaceutically acceptable salt thereof or a solvate thereof or a pharmaceutical composition comprising the compound for use in a method for treatment, preferably of the human or animal body, wherein the compound can be represented by the general structure of

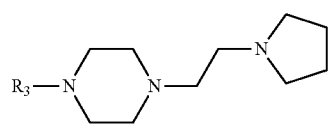

which can be preferably designated as 4-(2-pyrrolidin-1-yl-ethyl)piperazine and is selected from the group of compounds:

The present invention preferably relates to a compound or a pharmaceutically acceptable salt thereof or a solvate thereof or a pharmaceutical composition comprising the compound for use in a method for treatment, preferably of the human or animal body, wherein the compound can be represented by the general structure of

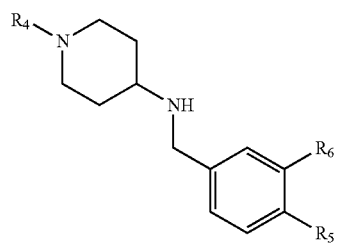

which can be preferably designated as benzyl-piperidin-4-yl-amine and is selected from the group of compounds:

1

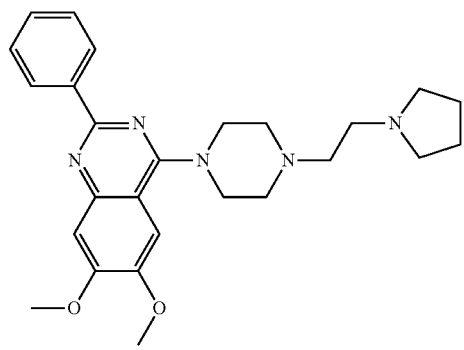

4

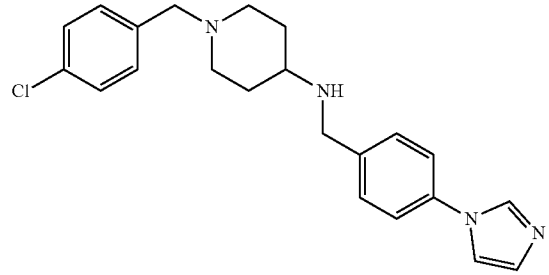

5

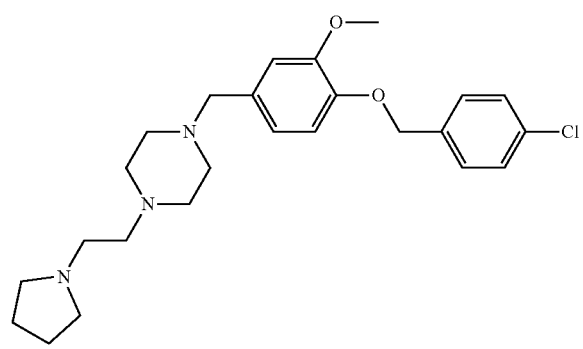

8

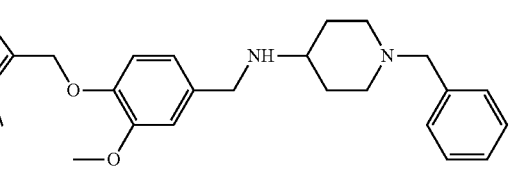

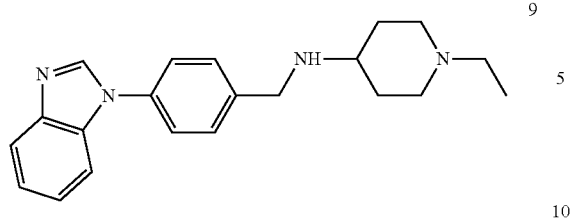
9
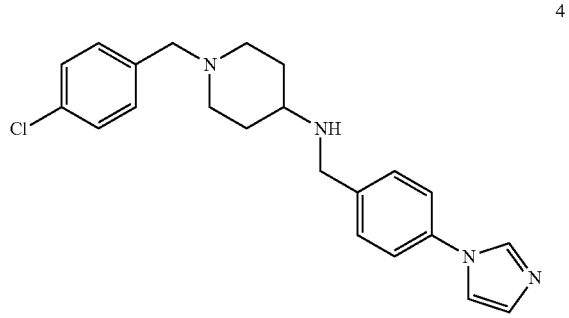
4
The present invention also relates to a toll-like receptor 9 (TLR9) antagonist or a pharmaceutically acceptable salt thereof or a solvate thereof, preferably being obtainable according to any one of the processes according to the present invention, preferably selected from the group of molecules as follows:
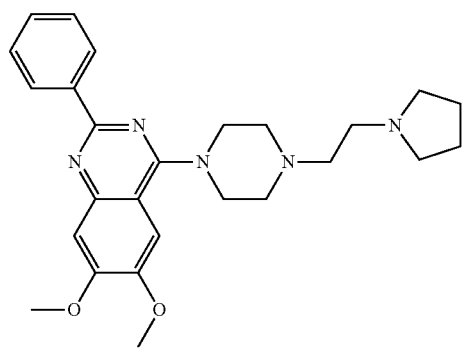
1
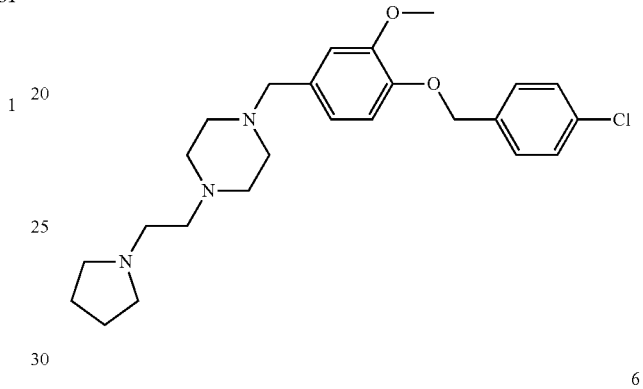
5
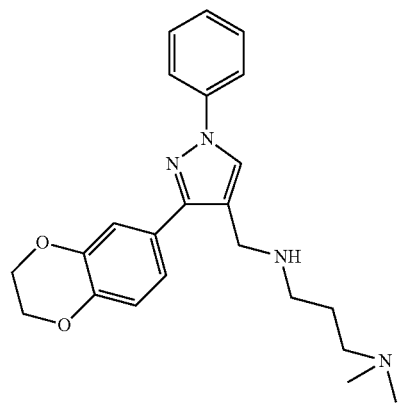
2
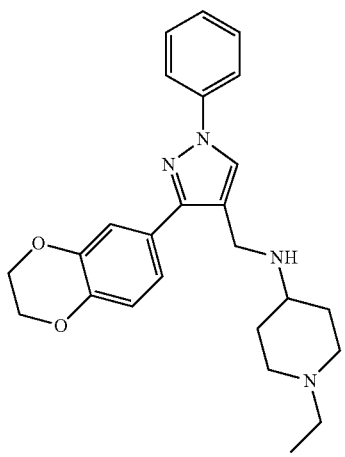
6
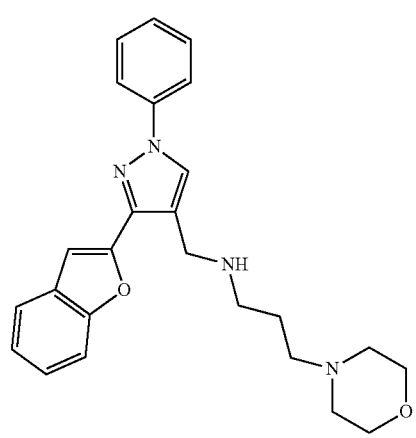
3
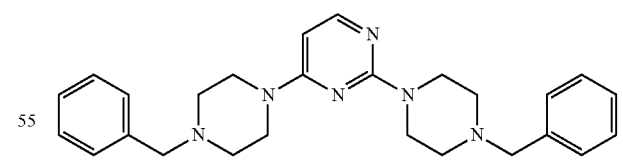
7
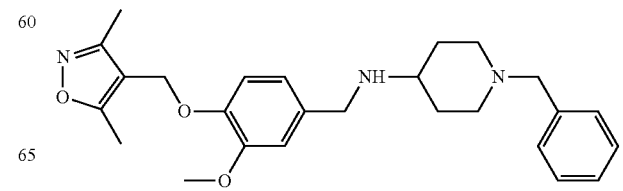
8

27
-continued
9
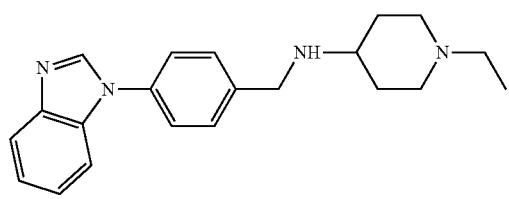
10
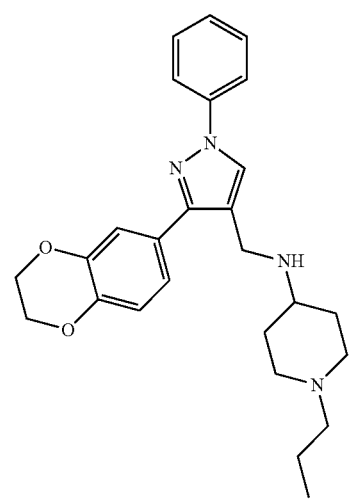
11
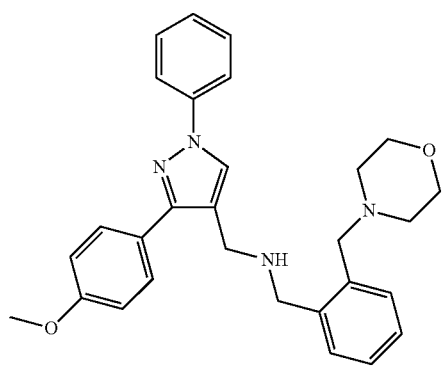
12
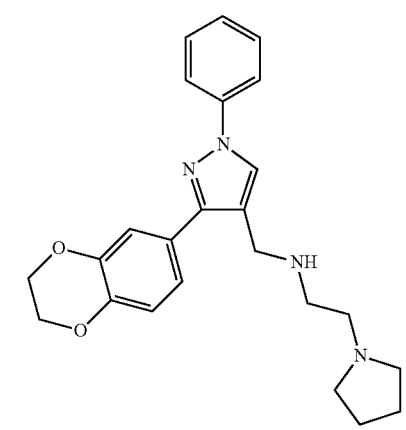
28
-continued
13
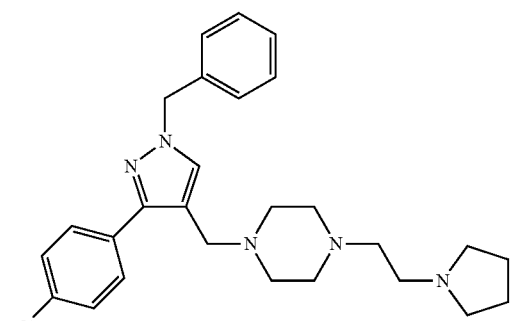
14
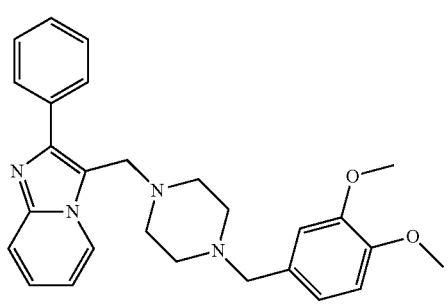
15
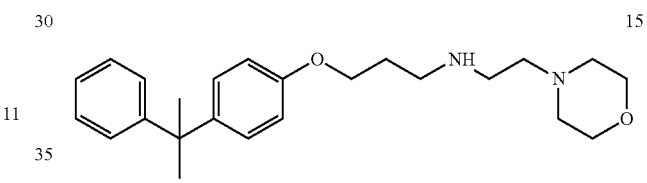
16
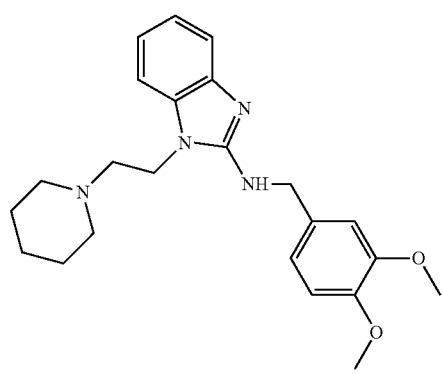
17
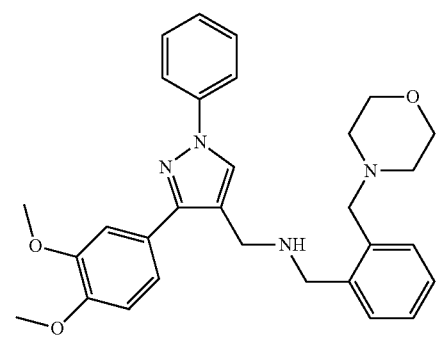

18

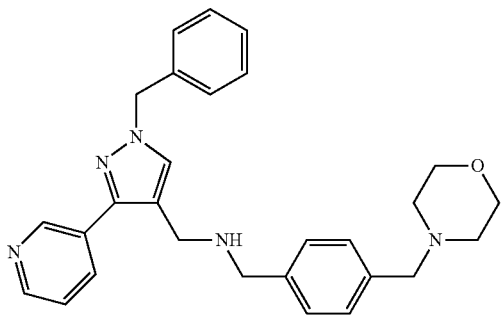

Preferably, the TLR9 antagonists from tables 5 and 7 are the subject-matter of the present invention. Preferably the TLR9 antagonists from tables 5 and 7 with an IC50 value of 500 μM or less, preferably 100 μM or less, preferably 20 μM or less, preferably 10 μM or less are the subject-matter of the present invention. Preferably, the TLR9 antagonists from table 7 are the subject-matter of the present invention. The present invention also relates to a pharmaceutical composition for use in a method of treating or preventing at least one disease with an excessive immune response, which comprises at least one toll-like receptor 9 (TLR9) antagonist according to the present invention or a pharmaceutically acceptable salt thereof or a solvate thereof. Accordingly, the TLR9 antagonists are the active ingredient in the treatment or prevention of the at least one disease with an excessive immune response.

Preferably, the compounds according to the present invention act as toll-like receptor 9 (TLR9) antagonists. Preferably, the compounds according to the present invention are used in therapy and/or prevention of a disease. Preferably, the compounds according to the present invention are used in a method for treatment of a disease, preferably of the human or animal body. Preferably, the compounds according to the present invention are used as medicament.

The term "TLR9 antagonist" preferably refers to a compound that is able to prevent or reduce immune stimulation mediated by TLR9.

The present invention preferably relates to pharmaceutical composition, which comprises further a pharmaceutically acceptable carrier.

The present invention also relates to a method of treatment or prevention of the at least one disease, preferably at least one disease with an excessive immune response, wherein at least one compound, preferably being the active ingredient and preferably acting as TLR9 antagonist, or pharmaceutical composition according to the present invention is administrated to a subject in need thereof. The at least one compound, preferably the TLR9 antagonist, is preferably administered as pharmaceutical composition as disclosed herein and preferably in a pharmaceutically, preferably therapeutically or prophylactically effective amount.

The term "subject" generally refers to a mammal, such as a human. Mammals generally include, but are not limited to, humans, non-human primates, rats, mice, cats, dogs, horses, cattle, cows, pigs, sheep and rabbits.

The term a "pharmaceutically effective amount" refers to an amount sufficient to affect a desired biological effect, such as a beneficial result, including, preferably prevention, inhibition, diminution, amelioration or elimination of signs or symptoms of a disease or disorder. Thus, a "pharmaceutically effective amount" will depend upon the context in which it is being administered. A pharmaceutically effective amount may be administered in one or more prophylactic or therapeutic administrations.

The term "prophylactically effective amount" refers to an amount sufficient to prevent, reduce or inhibit the development of an undesired biological effect, preferably a disease according to the present invention.

The term "therapeutically effective amount" refers to an amount sufficient to reduce or inhibit the undesired biological effect, preferably of a disease according to the present invention.

The term "solvate" is used herein in the conventional sense to refer to a complex of solute (e.g., active compound, salt of active compound) and solvent. If the solvent is water, the solvate may be conveniently referred to as a hydrate, for example, a hemihydrate, monohydrate, dihydrate, trihydrate, tetrahydrate, and the like. The solvate is preferably a hydrate.

A "pharmaceutically acceptable salt" is a salt in which the anion is not toxic to the human or animal body, preferably in the amount the compound, preferably the TLR9 antagonist is administrated to a subject in need thereof. Suitable anions are preferably fluoride, chloride, bromide, iodide, sulfate, bisulfate, nitrate, phosphate, citrate, methanesulfonate, trifluoroacetate, acetate, fumarate, oleate, valerate, maleate, oxalate, isonicotinate, lactate, salicylate, tartrate, tannate, pantothenate, bitartrate, ascorbate, succinate, gentisinate, gluconate, glucaronate, saccharate, formate, benzoate, glutamate, ethanesulfonate, benzenesulfonate, p-toluensulfonate, orpamoate.

A "pharmaceutically acceptable carrier" is a pharmaceutically acceptable solvent, suspending agent, or any other pharmacologically inert vehicle. Pharmaceutically acceptable carriers can be liquid or solid, and can be selected with the planned manner of administration in mind so as to provide for the desired bulk, consistency, and other pertinent transport and chemical properties. The pharmaceutically acceptable carriers are preferably selected from the group of water, saline solution, binding agents (preferably polyvinylpyrrolidone or hydroxypropyl methylcellulose), fillers (preferably lactose and other sugars, gelatin, or calcium sulfate); lubricants (preferably starch, polyethylene glycol, or sodium acetate); disintegrates (preferably starch or sodium starch glycolate); and wetting agents (preferably sodium lauryl sulfate).

The present invention provides preferably a method for reducing a TLR9-mediated immune response in a mammal, the method comprising administering to the mammal a compound or pharmaceutical composition according to the invention in an amount that reduces the TLR9-mediated immune response.

The invention preferably provides a method for therapeutically treating a mammal having a disease or disorder where reducing a TLR9-mediated immune response would be beneficial, preferably autoimmune disorders, airway inflammation, inflammatory disorders, allergy, asthma, arthritis, arthritis, malaria, allergy, transplant rejection, infectious disease, and other diseases and disorders that have an autoimmune component. Said method comprises preferably administering to the mammal having such a disorder or disease a compound or pharmaceutical formulation according to the invention in a therapeutically effective amount.

The invention preferably provides a method for preventing a disease or disorder in a mammal where reducing a TLR9-mediated immune response would be beneficial, preferably an autoimmune disorder, cancer, airway inflammation, inflammatory disorders, infectious disease, malaria, Lyme disease, ocular infections, skin disorders, psoriasis, scleroderma, cardiovascular disease, atherosclerosis, chronic fatigue syndrome, sarcoidosis, allergy, asthma or a disease caused by a pathogen. Said method preferably comprises administering to a mammal that is susceptible to such a disorder or disease a compound or pharmaceutical formulation according to the invention in a pharmaceutically effective amount.

The autoimmune disorder is preferably selected from lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis.

The inflammatory disorder is preferably selected from airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis and vasculitis.

The TLR9 antagonist compound can variously act by producing direct TLR9 antagonist effects alone and/or in combination with any other agent useful for treating or preventing the disease or condition that does not diminish the TLR9 antagonist effect of the compound. In any of the methods according to the invention, the agent(s) useful for treating or preventing the disease or condition includes, but is not limited to, vaccines, antigens, antibodies, preferably monoclonal antibodies, cytotoxic agents, allergens, antibiotics, siRNA, antisense oligonucleotides, other TLR agonist or antagonist (e.g. agonists or antagonists of TLR7, TLR8 and/or TLR3), chemotherapeutic agents (both traditional chemotherapy and modern targeted therapies), targeted therapeutic agents, activated cells, peptides, proteins, gene therapy vectors, peptide vaccines, protein vaccines, DNA vaccines, adjuvants, and co-stimulatory molecules (e.g. cytokines, chemokines, protein ligands, trans-activating factors, peptides or peptides comprising modified amino acids), or combinations thereof. Alternatively, the agent can include DNA vectors encoding for antigen or allergen. Alternatively, the compounds can be administered in combination with other adjuvants to enhance the specificity or magnitude of the immune response to the compound.

The administration of TLR9 antagonist compound, alone or in combination with any other agent, can be by any suitable route, including, without limitation, parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form. Administration of the therapeutic compositions of TLR9 antagonist compound can be carried out using known procedures using an effective amount and for periods of time effective to reduce symptoms or surrogate markers of the disease. For example, an effective amount of a TLR9 antagonist compound for treating a disease and/or disorder could be that amount necessary to alleviate or reduce the symptoms, or delay or ameliorate an autoimmune response. The effective amount for any particular application can vary depending on such factors as the disease or condition being treated, the particular oligonucleotide being administered, the size of the subject, or the severity of the disease or condition. One of ordinary skill in the art can empirically determine the effective amount of a particular compound according to the present invention without necessitating undue experimentation.

When administered systemically, the pharmaceutical, preferably therapeutic, composition is preferably administered at a sufficient dosage to attain a blood level of TLR9 antagonist from about 0.0001 micromolar to about 10 micromolar. For localized administration, lower concentrations than this dosage may be effective, and much higher concentrations may be tolerated. Preferably, a total dosage of TLR9 antagonist compound ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

The term "in combination with" generally means administering a compound according to the invention and another agent useful for treating the disease or condition that does not diminish TLR9 antagonist effect of the compound in the course of treating the same disease in the same patient. Such administration may be done in any order, including simultaneous administration, as well as temporally spaced order from a few seconds up to several days apart. Such combination treatment may also include more than a single administration of the compound according to the invention and/or independently the other agent. The administration of the compound according to the invention and the other agent may be by the same or different routes.

The term "allergy" generally includes, without limitation, food allergies, respiratory allergies, and skin allergies.

The term "antigen" generally refers to a substance that is recognized and selectively bound by an antibody or by a T cell antigen receptor. Antigens may include but are not limited to peptides, proteins, nucleosides, nucleotides and combinations thereof. Antigens may be natural or synthetic and generally induce an immune response that is specific for that antigen.

The term "autoimmune disorder" refers to disorders in which "self" antigen undergoes attack by the immune system.

The term "allergen" refers to an antigen or antigenic portion of a molecule, usually a protein, which elicits an allergic response upon exposure to a subject. Typically, the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule. The present invention also relates to a toll-like receptor 9 (TLR9) antagonist according to the present invention for use in a method of treating or preventing at least one, preferably exactly one, disease with an excessive immune response, which is preferably TLR9-mediated.

The present invention also relates to a compound, preferably a toll-like receptor 9 (TLR9) antagonist, according to the present invention for use in a method of treating or preventing at least one, preferably exactly one, TLR9-mediated immune response disease in a mammal.

The disease, preferably the TLR9-mediated immune response disease, is preferably autoimmune disorder, airway inflammation, inflammatory disorders, allergy, asthma, arthritis, arthritis, malaria, allergy, transplant rejection, infectious disease, and other diseases and disorders that have an autoimmune component.

Preferably, the disease, preferably the TLR9-mediated immune response disease, is an autoimmune disorder, cancer, airway inflammation, inflammatory disorders, infectious disease, malaria, Lyme disease, ocular infections, skin disorders, psoriasis, scleroderma, cardiovascular disease, atherosclerosis, chronic fatigue syndrome, sarcoidosis, allergy, asthma or a disease caused by a pathogen.

The autoimmune disorder is preferably selected from lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis.

The inflammatory disorder is preferably selected from airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis and vasculitis.

The present invention preferably relates to a toll-like receptor 9 (TLR9) antagonist according to the present invention for use in a method of treating or preventing disease with an excessive immune response, wherein the disease with an excessive immune response is selected from TLR9-mediated autoimmune diseases, transplant rejection, and sepsis.

The present invention preferably relates to toll-like receptor 9 (TLR9) antagonist according to the present invention for use in a method of treating or preventing at least one disease with an excessive immune response, wherein the disease with an excessive immune response is selected from lupus erythematosus, multiple sclerosis, rheumatoid arthritis, atopic dermatitis, psoriasis, hyperlipidaemia, atherosclerosis and human sepsis.

Preferred embodiments of the present invention are the subject-matter of the sub-claims.

DRAWINGS

The present invention is illustrated by the following figures and examples.

Figure 3:
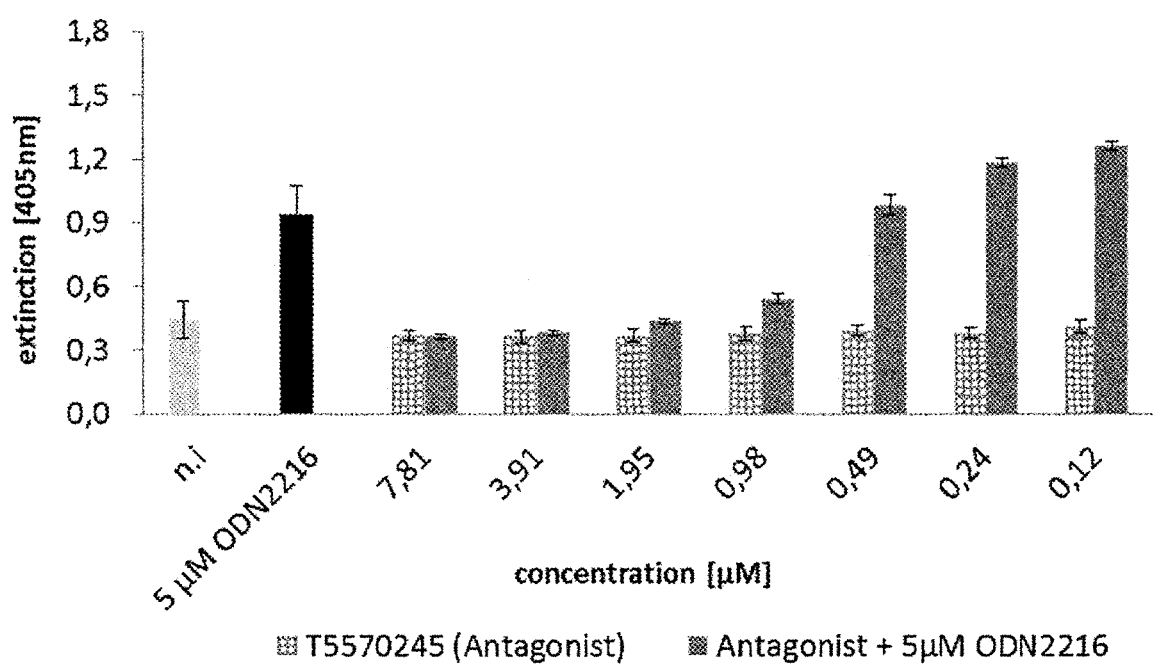

FIG. 3 shows IC50 value measuring of antagonist T5570245 (3; Enamine name) in presence of ODN 2216 agonist. Inhibition is done using 5 µM concentrations of ODN 2216 and with 0.12 µM-7.8 µM of antagonist. There is dose dependent reduction of the signal: increased antagonist concentration leads to a reduced ODN2216 signal. IC50 value was determined as 0.8 µM.

DETAILED DESCRIPTION

Examples

1. Data Preparation—Building/Training ISE Models 239 biology active ligands for the *Homo Sapiens* TLR9 receptor with IC50 values in the range of 20 nM to 49782 nM were retrieved from ChEMBL database (Gaulton, A.; Bellis, L. J.; Bento, A. P.; Chambers, J.; Davies, M.; Hersey, A.; Light, Y.; McGlinchey, S.; Michalovich, D.; Al-Lazikani, B., ChEMBL: a large-scale bioactivity database for drug discovery. Nucleic Acids Res. 2012, 40 (D1), D1100-D1107). Additional 59 inhibitors with values in the range of 3.4 nM to 250 nM were found in patents (WO 2010/036905; WO 2005/007672; WO 2008/030455). Inhibitors without specified IC50 values were not included in the group of active molecules. This results in 289 known inhibitors.

Optionally, the group of 289 known inhibitors were "washed" of counter-ions by using the WASH application of the MOE software (Molecular Operating Environment (MOE), 2013.08, Chemical Computing Group Inc.: 1010 Sherbooke St. West, Suite #910, Montreal, QC, Canada, H3A 2R7, 2013) and prepared as the "actives" database, also termed as group of known active molecules.

For the "inactive" class, also termed as group of inactive molecules, 10.000 molecules from the Enamine database (Enamine Ltd. Screening compound Provider at http://www.enamine.net/) were picked randomly after filtering the database according to the "Applicability Domain" of the actives, which is the average value of some parameters plus/minus two standard deviations from the average, wherein the parameters are preferably selected from the group of molecular weight, log P (logarithm of partition coefficient), number of hydrogen bond donors and number of hydrogen bond acceptors.

In order to avoid bias due to molecules that are very similar (Tanimoto coefficient is about 1) solely active molecules that have Tanimoto coefficient of 0.7 and less vis-à-vis each other were used as 'actives', so that they are substantially different. If initially two molecules with a Tanimoto coefficient of greater than 0.7 were present in the group of active molecules, the molecule with the higher IC50 value was kept.

The Tanimoto filtration resulted in 151 molecules with only 7 molecules with IC50 below 1500 nM. The decision was to build two ISE models with two different initial sets: the first set—the Tanimoto "filtered" set with 151 active molecules but mostly with low IC50 value, and the second "full" set with all the 289 actives without any Tanimoto similarity filtering, which includes 54 molecules with IC50 values below 400 nM.

Physico-chemical descriptors for the 151 active molecules of the "filtered" set and for the 289 active molecules of the "full" set were calculated. In order to avoid bias and difficulties in interpretations, highly correlated descriptors were eliminated based on the Linear Correlation Matrix produced by KNIME software. Subsequently, 118 descriptors remained in the "filtered" set and 108 descriptors remained in the "full" set of active molecules.

These remaining descriptors were subsequently calculated for the ten thousand randomly picked inactives taken from the Enamine database.

Subsequently, two ISE models each having a set of filters were generated, one for the "full" set of actives and one for the "Tanimoto filtered" set of actives.

A five-fold partition was employed in generating both ISE models.

As a first level of validation, filters generated for the learning sets which include all the 9999 inactives and the 289 actives ("full set") and, respectively, 151 actives ("Tanimoto filtered set") of the five-fold modeling process were combined and Indexes by the ISE model were given to each molecule in each of the ISE models.

Results for the "Tanimoto filtered set" are shown in table 1 and results for the full set are shown in table 2. In both of these tables and the successive tables, each ISE index number represents a separation between those that are "negatives" (i.e., assumed to be inactive or less actives) with lower indexes while those that are with higher indexes are assumed to be "actives". This leads also to the clear assignment of "true" and "false" actives and inactive or less actives. For example, in table 1, the line at an ISE index of 0.3 shows that 9756 (out of the total 9999 inactives) are found with lower indexes. Thus, at this separation, they will be assumed to be TN, true negatives while the rest, 241 inactives, have higher indexes and are thus wrongly assumed to be actives, thus being false positives (FP). For the actives, there are 117 found at that level with lower indexes thus being false negatives (FN) while 34 are above that index values, thus TP, true positives. From those 4 numbers it is possible to construct the MCC score (Stern, N.; Goldblum, A., Iterative stochastic elimination for solving complex combinatorical problems in drug discovery. Israel Journal of Chemistry. 2014, 54 (8-9), 1338-1357) which gives an idea of the quality of that particular separation.

The "enrichment" at each separation line depends on TP/P (true positives out of the total positives (sum of TP and FP (false positives))) divided by the chance to find that ratio, which is the ratio of the actives to the total training set. Thus at the 0.3 index line of table 1, the enrichment is (34/275)/(151/10150)=8.3. It is increased at the separation line of index 0.5 to 10.1 and of index=0.6 to 10.9.

The 'enrichment' is defined as true positives out of the total positives divided by the chance to find said ratio, which is the ratio of actives in the total training sets consisting of the group of active molecules and the group of inactive and/or less active molecules.

$$E = \frac{TP/TP+FP}{A/A+IA}$$

TP=true positives; FP=false negatives; A=active molecules; IA=inactive or less active molecules.

TABLE 1

| ISE index border | TN | FN | TP | FP | MCC |
|---|---|---|---|---|---|
| 0 | 9500 | 92 | 59 | 499 | 0.181 |
| 0.1 | 9595 | 102 | 49 | 403 | 0.1668 |
| 0.2 | 9683 | 108 | 43 | 316 | 0.1659 |
| 0.3 | 9756 | 117 | 34 | 241 | 0.1499 |
| 0.4 | 9841 | 123 | 28 | 158 | 0.1531 |
| 0.5 | 9903 | 134 | 17 | 96 | 0.1188 |
| 0.6 | 9968 | 145 | 6 | 31 | 0.0736 |
| 0.7 | 9999 | 151 | 0 | 0 | — |

TABLE 2

| ISE index border | TN | FN | TP | FP | MCC |
|---|---|---|---|---|---|
| 0 | 9831 | 217 | 72 | 167 | 0.255 |
| 0.1 | 9856 | 226 | 63 | 143 | 0.2403 |
| 0.2 | 9901 | 237 | 52 | 98 | 0.2345 |
| 0.3 | 9927 | 242 | 47 | 72 | 0.2402 |
| 0.4 | 9947 | 253 | 35 | 52 | 0.2096 |
| 0.5 | 9959 | 277 | 12 | 39 | 0.0885 |
| 0.6 | 9999 | 289 | 0 | 0 | — |

For the "full" set, with no Tanimoto filtering, the results are a bit better in terms of enrichment. At the separation level 0.4, the enrichment is about 14. It is lower in the next index level of 0.5, going down to about 8.

If all the filters, about 2500 from all the 5-fold runs are combined, and the full learning set is screened through those filters, an interesting result were obtained (table 3), taking the "separating line" at an index of 0.4.

TABLE 3

| ISE index border | TN | FN | TP | FP | MCC |
|---|---|---|---|---|---|
| 0 | 9335 | 210 | 79 | 65 | 0.375 |
| 0.1 | 9473 | 225 | 64 | 27 | 0.386 |
| 0.2 | 9987 | 236 | 53 | 13 | 0.377 |
| 0.3 | 9996 | 252 | 37 | 4 | 0.335 |
| 0.4 | 10000 | 260 | 29 | 0 | 0.313 |
| 0.5 | 10000 | 289 | 0 | 0 | — |

The differentiation between TP and FP with said ISE model is very good. There are 29 true positives, and no false positives, meaning no observed false positives above the ISE index of 0.4, when using all the five sets of generated filters together.

Due to the fact that the MCC score for each threshold of the "full" set were higher than those of the "filtered" set, in addition to the greater enrichment values (above 35 at the ISE index of 0.4) and as the filters of the "Tanimoto filtered" set gave false predictions for 26 out of the 41 best rated molecules (not shown) it was decided to proceed with the "full" model for screening search molecules.

2. Screening of External Databases

Figure 1:
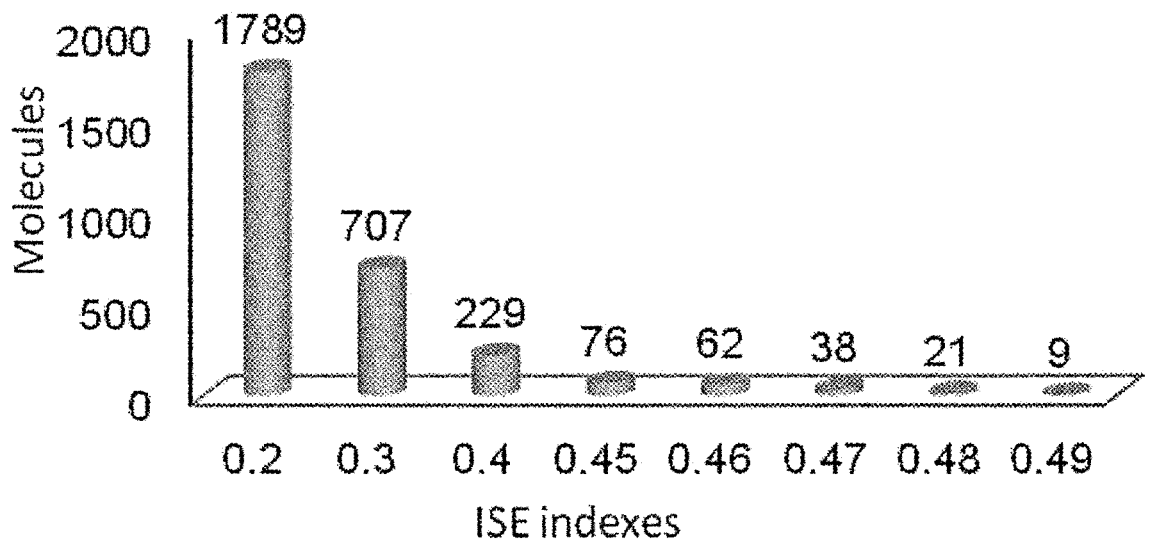
FIG. 1 shows ISE indexing results after applying the "full" ISE model filtering to a group of search molecules.

The Enamine database containing about 1.8 million molecules was virtually screened using the ISE "full" model. The scan finds a large amount of 1789 molecules with activity indexes above 0.2 as seen in FIG. 1.

Figure 2:
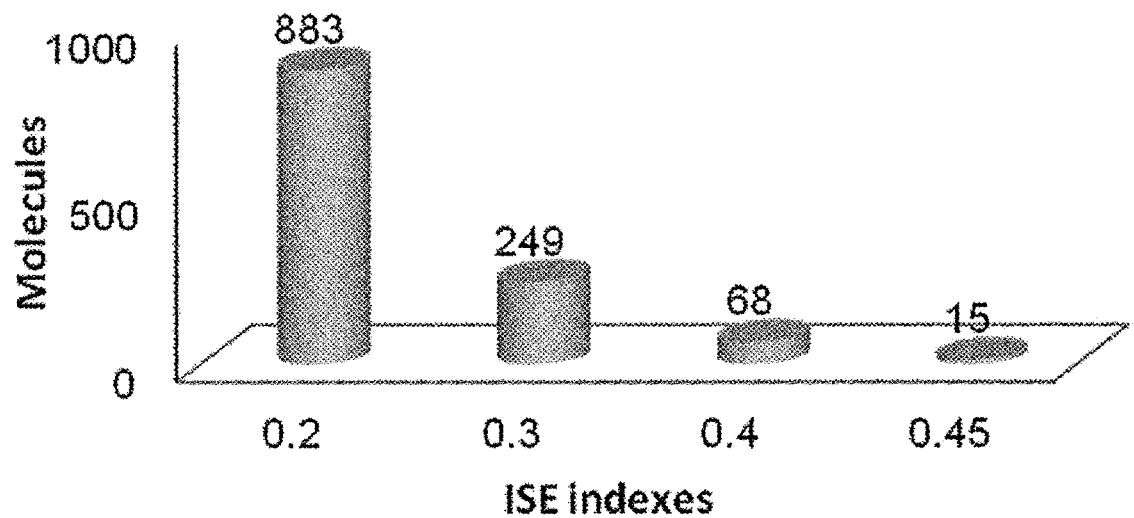
FIG. 2 shows ISE indexing results after applying the "applicability domain" filtering to a group of target molecules.

These molecules were filtered using the "applicability domain" of the TLR9 inhibitors. The results are shown in FIG. 2.

For the 68 molecules with ISE indexes above 0.4, aqueous solubility values were calculated using the following five different software programmes.

The VCCLAB program calculates aqueous solubility (ALOGpS), called log S VCCLAB in table 4, based on 1291 known soluble molecules and provides aqueous solubility predictions using Artificial Neural Networks (Virtual Computational Chemistry Laboratory VCCLAB: ALOGPS 2.1 Software at http://www.vcclab.org/lab/alogps/).

The LMMD developed solubility calculations, called log S admetSAR in table 4, using two aqueous solubility models: ASMS (aqueous solubility based on molecular surface) and ASMSLOGP (aqueous solubility based on molecular surface using C log P as a descriptor) (Laboratory of Molecular Modeling and Design (LMMD): admetSAR tool Software at http://www.admetexp.org/).

The SciFinder software (of the American Chemical Society) calculates Molar Intrinsic Solubility via Advanced Chemistry Development (ACD/Labs) Software V11.02, called log S SciFinder in table 4 (SciFinder Software at https://scifinder.cas.org).

Additional solubility values, called log S MOE and Log S Enamine in Table 4, were retrieved with MOE program (Molecular Operating Environment (MOE), 2013.08, Chemical Computing Group Inc.: 1010 Sherbooke St. West, Suite #910, Montreal, QC, Canada, H3A 2R7, 2013) and Enamine software (Enamine Ltd. Screening compound Provider at http://www.enamine.net/).

A standard deviation for the different solubility values for each candidate was calculated, and 30 molecules with lowest standard deviation which showed good solubility for at least 3 out of 5 solubility values were selected for subsequent in vitro testing.

TABLE 4

| Enamine name | ISE index | logS MOE | logS VCCLAB | logS admetSAR | logS SciFinder | logS Enamine | deviation logS | in vitro testing |
|---|---|---|---|---|---|---|---|---|
| T0400-0929 | 0.426 | −4.89 | −7.25 | −3.70 | — | −10.078 | 23.77 | |
| T0400-1399 | 0.43 | −5.05 | −5.33 | −4.22 | −5.55 | −6.79 | 3.47 | |
| T0501-0693 | 0.408 | −3.95 | −5.45 | −3.43 | −3.70 | −4.441 | 2.53 | + |
| T0501-1111 | 0.408 | −4.26 | −5.77 | −3.59 | −3.74 | −5.079 | 3.40 | + |
| T0501-2395 | 0.401 | −6.72 | −5.62 | −3.96 | −6.01 | −6.03 | 4.27 | |
| T0501-8198 | 0.413 | −6.57 | −5.86 | −4.15 | −6.14 | −6.27 | 3.65 | |
| T0502-6618 | 0.435 | −5.42 | −4.56 | −3.86 | −4.48 | −6.78 | 5.11 | |
| T0502-6934 | 0.456 | −4.74 | −4.51 | −3.21 | −5.39 | −5.68 | 3.69 | + |
| T0504-1221 | 0.453 | −5.76 | −4.68 | −3.08 | −4.83 | — | 3.71 | + |
| T0504-1257 | 0.486 | −5.47 | −5.46 | −3.78 | −4.77 | −5.20 | 1.99 | + |
| T0504-3143 | 0.404 | −5.50 | −4.31 | −2.55 | −4.82 | −8.51 | 18.99 | |
| T0504-8410 | 0.41 | −5.86 | −5.06 | −2.22 | −6.51 | −7.29 | 15.25 | |
| T0505-2171 | 0.401 | −4.11 | −4.22 | −2.35 | −4.39 | −6.01 | 6.72 | + |
| T0505-2234 | 0.401 | −5.48 | −4.87 | −2.82 | −5.42 | −6.30 | 6.89 | |
| T0506-4124 | 0.403 | −4.30 | −4.69 | −3.58 | −5.02 | −5.68 | 2.45 | + |
| T0508-4302 | 0.445 | −5.57 | −6.24 | −3.62 | −4.80 | −6.15 | 4.74 | |
| T0509-4572 | 0.454 | −6.12 | −5.47 | −3.13 | −5.33 | −6.11 | 6.03 | |
| T0510-1916 | 0.454 | −5.52 | −6.24 | −4.25 | −4.68 | −6.57 | 3.92 | |
| T0513-2251 | 0.407 | −4.25 | −4.38 | −3.37 | −4.21 | −5.69 | 2.80 | + |
| T0513-3871 | 0.486 | −5.51 | −5.6 | −3.12 | −5.72 | −5.63 | 5.00 | |
| T0513-5752 | 0.473 | −4.98 | −4.15 | −2.71 | −3.70 | −5.04 | 3.74 | + |
| T0518-7930 | 0.419 | −5.40 | −4.88 | −4.69 | −5.30 | −8.69 | 10.82 | |
| T0519-4581 | 0.414 | −5.72 | −3.77 | −3.10 | −7.85 | −5.04 | 13.74 | + |
| T0520-3191 | 0.41 | −6.46 | −4.64 | −4.16 | −5.27 | −6.54 | 4.54 | |
| T5232381 | 0.448 | −6.81 | −4.45 | −2.84 | −5.59 | −8.22 | 17.23 | |
| T5443186 | 0.411 | −5.36 | −4.23 | −3.66 | −5.74 | −6.08 | 4.23 | |
| T5443257 | 0.411 | −5.37 | −4.16 | −3.45 | −5.68 | −6.15 | 5.02 | |
| T5444954 | 0.419 | −6.33 | −5.13 | −3.13 | −5.00 | −6.68 | 7.78 | |
| T5456813 | 0.454 | −5.80 | −3.89 | −3.39 | −4.64 | −5.26 | 3.84 | + |
| T5457553 | 0.425 | −6.28 | −5 | −3.21 | −5.15 | −5.21 | 4.92 | |
| T5500062 | 0.414 | −4.70 | −4.77 | −4.34 | −4.44 | −5.87 | 1.51 | + |
| T5547436 | 0.429 | −4.13 | −3.06 | −2.47 | −3.00 | −6.20 | 8.82 | + |
| T5666774 | 0.415 | −5.59 | −3.85 | −2.86 | −7.35 | −5.59 | 12.08 | + |
| T5702130 | 0.401 | −4.47 | −5.28 | −3.24 | −4.59 | −5.27 | 2.78 | + |
| T5713724 | 0.401 | −4.47 | −5.28 | −3.32 | −4.64 | −5.37 | 2.72 | + |
| T5733268 | 0.415 | −5.61 | −5.7 | −3.33 | −5.68 | −7.12 | 7.40 | |
| T5762626 | 0.486 | −5.54 | −5.67 | −2.97 | −5.11 | −5.27 | 4.89 | + |
| T5771455 | 0.459 | −5.00 | −4.23 | −3.44 | −4.92 | −4.82 | 1.73 | + |
| T5771817 | 0.413 | −5.74 | −6.19 | −3.93 | −5.44 | −7.91 | 8.20 | |
| T5771936 | 0.435 | −4.36 | −4.26 | −2.93 | −3.48 | −5.26 | 3.18 | + |
| T5771955 | 0.411 | −3.92 | −4.13 | −2.86 | −4.00 | −4.90 | 2.14 | + |
| T5772747 | 0.412 | −6.62 | −3.56 | −2.49 | −5.28 | −7.29 | 16.29 | |
| T5772784 | 0.439 | −5.21 | −5.65 | −3.94 | −4.96 | −6.47 | 3.46 | |
| T5772868 | 0.486 | −5.97 | −4.96 | −3.46 | −5.00 | −6.32 | 4.94 | |
| T5772891 | 0.413 | −5.74 | −6.24 | −3.93 | −5.44 | −7.75 | 7.60 | |
| T5772898 | 0.439 | −5.41 | −5.95 | −3.81 | −5.30 | −7.12 | 5.72 | |
| T5793004 | 0.439 | −5.41 | −5.92 | −3.81 | −5.30 | −7.13 | 5.73 | |
| T5793086 | 0.413 | −4.45 | −4.9 | −3.20 | −4.68 | −6.05 | 4.17 | |
| T5803292 | 0.456 | −5.16 | −4.48 | −4.09 | −4.51 | −5.58 | 1.41 | + |
| T5806616 | 0.439 | −5.41 | −5.9 | −3.69 | −5.10 | −7.14 | 6.27 | |
| T5807811 | 0.414 | −5.71 | −4.99 | −2.02 | −6.11 | −5.26 | 10.53 | + |
| T5869849 | 0.413 | −6.78 | −5.05 | −3.27 | −4.48 | −6.86 | 9.45 | |
| T5922759 | 0.4 | −4.98 | −3.29 | −3.20 | −3.96 | −5.72 | 4.80 | + |
| T6009038 | 0.434 | −7.29 | −4.54 | −2.87 | −5.36 | −7.00 | 13.25 | |
| T6009051 | 0.437 | −6.54 | −4.2 | −2.58 | −5.11 | −5.55 | 8.94 | |
| T6015017 | 0.437 | −6.26 | −4.6 | −2.92 | −4.48 | −5.98 | 7.21 | + |
| T6017130 | 0.451 | −6.73 | −4.99 | −3.27 | −4.30 | −6.25 | 7.97 | |
| T6021435 | 0.413 | −6.63 | −5.06 | −3.51 | −3.82 | −6.75 | 9.20 | |
| T6123818 | 0.401 | −4.95 | −5.77 | −3.55 | −4.74 | −5.85 | 3.47 | |
| T6306924 | 0.486 | −5.54 | −5.7 | −3.42 | −4.89 | −5.29 | 3.37 | + |
| T6416309 | 0.422 | −4.00 | −4.2 | −3.10 | −4.10 | −5.22 | 2.27 | + |
| T6416601 | 0.486 | −6.15 | −4.97 | −3.58 | −4.85 | −5.87 | 4.09 | |
| T6495030 | 0.43 | −4.08 | −2.99 | −2.71 | −2.82 | −5.98 | 7.58 | + |
| T6549007 | 0.403 | −4.59 | −4.84 | −2.85 | −3.72 | −5.37 | 3.95 | + |
| T6593995 | 0.438 | −5.68 | −3.62 | −2.86 | −8.00 | −4.81 | 16.02 | + |

TABLE 4-continued

| Enamine name | ISE index | logS MOE | logS VCCLAB | logS admetSAR | logS SciFinder | logS Enamine | deviation logS | in vitro testing |
|---|---|---|---|---|---|---|---|---|
| T6747644 | 0.422 | −5.55 | −3.35 | −1.92 | −5.34 | −7.05 | 16.21 | |
| T6881142 | 0.414 | −5.09 | −6.12 | −3.42 | −4.92 | −6.76 | 6.52 | |
| T6895608 | 0.401 | −4.47 | −5.26 | −3.30 | −4.36 | −5.20 | 2.52 | + |

3. Measuring of the Potential Antagonists to Determine the IC50 Values Using a Cell-Based Reporter Assay A cell based test-system that allows PAMPs to be identified and differentiated via pattern recognition receptors (PRRs) in a reporter gene assay was used (DE 10 2006 031 483, EP 2 041 172). For this assay human PRRs and co-receptors were stably transfected and expressed in NIH 3T3 fibroblasts. This cell line expresses no other PRRs and contains a reporter gene which is activated by PRR-activation. The induction of receptor complexes by their ligands leads, after a signalling cascade, to an activation of transcription factor NF-kB, which regulates the expression of an additional integrated reporter gene, a secreted alkaline phosphatase (SEAP) (Burger-Kentischer, A.; Abele, I. S.; Finkelmeier, D.; Wiesmüller, K.-H.; Rupp, S., A new cell-based innate immune receptor assay for the examination of receptor activity, ligand specificity, signalling pathways and the detection of pyrogens. J. Immunol. Methods 2010, 358 (1), 93-103).

This test system mimics elements of the innate human immune system and can selectively recognize a large number of PAMPs with high sensitivity. Consequently, the PRR-specific cell-based high-throughput feature of the reporter cell lines will provide a fast, flexible and convenient means for lead compound screening in the pharmaceutical drug development fields. For the in vitro screening of the top candidates identified at IDR, the Fraunhofer IGB used this cell-based reporter system to identify TLR9 antagonists in order to determine their activity as well their biocompatibility. Within a first step the NIH3T3 cell line expressing TLR9 was used to measure the inhibitory effect of the TLR9 antagonists.

For the experiment the reporter cell line expressing TL9 was plated in 96-well cell culture plates at a density of $0.3 \times 10^5$ cells in DMEM media supplemented with 10% FCS (Invitrogen), 1% L-glutamine (200 mM Invitrogen) and 1% Penicillin-Streptomycin (PenStrep: 100×, Invitrogen). The cells were incubated for 16 h to grow adherent monolayers at 37° C. in a 5% saturated CO2 humidified atmosphere. After overnight incubation, the media was removed and replaced by DMEM medium supplemented with 1% PenStrep, 1% L-glutamine and 0.5% FCS. The media change is important to avoid a unspecific background signal, caused by active remaining phosphatases present in the FCS. The cells are then stimulated with a specific ligand non-methylated CpG ODN 2216 agonist (Invivogen) and the potential antagonists using different concentrations, namely within a range of concentrations of the potential antagonists starting with 0.025 µM (for the antagonist with the highest activity) up to 14 mM for the antagonists with lowest activities.

The ODN ligand has the sequence 5'-ggGG GACGA:TCGTCgggggg-3' (SEQ ID No. 1). Those represented by capital letters are phosphodiesters, and those in small letters are phosphorothioate. The Palindrome is underlined.

The cells were again incubated in a humidified atmosphere for 16h leading to the expression or reduced expression of SEAP and its secretion into the media. Binding of the antagonist leads to a block of the TLR9, resulting in no or in a reduced expression of the reporter gene (SEAP). Therefore, 50 µl supernatant were taken from the cells and transferred into a 96-well PS microplate flat bottom (Greiner BIO-ONE). The enzyme substrate reaction was initiated by adding 50 µl of the specific substrate. SEAP catalyses the hydrolysis of pNPP to the final product para-nitrophenol (yellow), which can be detected in a photometric analysis using an UV-VIS reader at 405 nm. The results of the measurements were fed back to the IDR for further optimization of the structure. All results are based on n≥3 experiments and were illustrated in graphs (OD405 nm values) and the IC50 was calculated. The values were presented as mean±SEM.

The in vitro testing of the 30 candidates for TLR9 inhibition resulted in 9 molecules with IC50 values in the range of 7.27-30.34 µM (table 5), while 26 of these 30 candidates showed TLR9 inhibition activity. Thus, further improvement of those candidates is required. As example for measuring the activity of substrate T5570245 (3) is shown in FIG. 3. The IC50 values of the 30 screened compounds shown at table 5.

TABLE 5

| Enamine name | ISE index | Smiles | Mol. Weight | logS Enamine | IC50 in [µM] |
|---|---|---|---|---|---|
| T0501-0693 | 0.408 | O(C)c1ccc(\N=C\c2cc3c(nccc3)cc2)cc1 | 262.31 | −4.441 | 15.72 |
| T0501-1111 | 0.408 | O(C)c1ccc(cc1)\C=N\c1cc2c(nc(cc2)C)cc1 | 276.34 | −5.079 | 487.89 |
| T0502-6934 | 0.456 | n1c2n(cc1-c1ccccc1)-c1c(CC2)ccc2c1nccc2 | 297.36 | −5.68 | 13232.29 |
| T0504-1221 | 0.453 | O(C)c1cc2nc3-c4c5c(-c3nc2cc1)cccc5ccc4 | 284.32 | −4.83 | 65.58 |
| T0504-1257 | 0.486 | n1c2c(nc(c1-c1ccccc1)-c1ccccc1)cccc2 | 282.35 | −5.20 | 1986.88 |
| T0505-2171 | 0.401 | N(/N1CCN(CC1)c1ccc(cc1)C)=C\C=C\c1ccccc1 | 305.42 | −6.01 | agonist |
| T0506-4124 | 0.403 | n1c2c(ccc1\C=C\c1ccc(N(C)C)cc1)cccc2 | 274.37 | −5.68 | 312 |
| T0513-2251 | 0.407 | O(CCOc1c2ncccc2ccc1)c1ccccc1OCC | 309.36 | −5.69 | 1075.88 |
| T0513-5752 | 0.473 | O1CCN(CC1)c1nc2c(ccc(OC)c2)c(c1)-c1ccccc1 | 320.39 | −5.04 | 7.77 |
| T0519-4581 | 0.414 | o1c2c(ncnc2N(CCc2cc(OC)c(OC)cc2)C)c2c1cccc2 | 363.42 | −5.04 | 15.06 |
| T5456813 | 0.454 | o1cccc1-c1nc2c(n1CCOc1ccccc1)cccc2 | 304.35 | −5.26 | 73.21 |
| T5500062 | 0.414 | n1c2c(ccc1\C=C\c1ccc(-n3ccnc3)cc1)cccc2 | 297.36 | −5.87 | 777.09 |
| T5547436 | 0.429 | O(C)c1ccccc1N1CCN(CC1)c1nc2c(cc1)cccc2 | 319.41 | −6.20 | 1160.88 |
| T5666774 | 0.415 | o1c2c(ncnc2NCCc2cc(OC)c(OC)cc2)c2c1cccc2 | 349.39 | −5.59 | 30.34 |
| T5702130 | 0.401 | O(C)c1cc(cc(OC)c1)\C=C\c1nc2c(cc1)cccc2 | 291.35 | −5.27 | 7.27 |

TABLE 5-continued

| Enamine name | ISE index | Smiles | Mol. Weight | logS Enamine | IC50 in [µM] |
|---|---|---|---|---|---|
| T5713724 | 0.401 | O(C)c1cc(OC)ccc1\C=C\c1nc2c(cc1)cccc2 | 291.35 | −5.37 | 15.93 |
| T5762626 | 0.486 | n1c2c(cccc2)c(cc1-c1cccnc1)-c1cccccc1 | 282.35 | −5.27 | agonist |
| T5771455 | 0.459 | O(C)c1ccc(-n2c3c(nc2-c2ccncc2)cccc3)cc1 | 301.35 | −4.82 | 11.93 |
| T5771936 | 0.435 | O(CCCn1ccnc1)c1ccc(cc1)-c1cccccc1 | 278.35 | −5.26 | — |
| T5771955 | 0.411 | O(CCOc1ccc(OC)cc1)c1c2ncccc2ccc1 | 295.34 | −4.90 | 650.23 |
| T5803292 | 0.456 | n1c2c(cccc2)c(cc1-c1ccc(-n2ccnc2)cc1)C | 285.35 | −5.58 | 4272.88 |
| T5807811 | 0.414 | n1cnc2c(cccc2)c1NCCNc1c2c(ccc1)cccc2 | 314.39 | −5.26 | 56.99 |
| T5922759 | 0.4 | Clc1cc(N2CCN(CC2)c2ncnc3c2cccc3)ccc1 | 324.81 | −5.72 | — |
| T6015017 | 0.437 | O(C)c1ccc(-n2cc(c3c2ncnc3NCCOC)-c2cccccc2)cc1 | 374.44 | −5.98 | 2028.86 |
| T6306924 | 0.486 | n1c2c(cccc2)c(cc1-c1ccncc1)-c1cccccc1 | 282.35 | −5.29 | 870.3 |
| T6416309 | 0.422 | O(CCCCn1c2c(nc1)cccc2)c1cc(OC)ccc1 | 296.37 | −5.22 | 13.26 |
| T6495030 | 0.43 | n1c2c(ccc1N1CCN(CC1)c1cccccc1)cccc2 | 289.38 | −5.98 | 219.55 |
| T6549007 | 0.403 | O1CCN(CC1)c1ccc(cc1)\C=C\c1nc2c(cc1)cccc2 | 316.40 | −5.37 | 4319.52 |
| T6593995 | 0.438 | o1c2c(ncnc2N(CCOc2ccc(OC)cc2)C)c2c1cccc2 | 349.39 | −4.81 | 904.6 |
| T6895608 | 0.401 | O(C)c1cc(ccc1OC)\C=C\c1nc2c(cc1)cccc2 | 291.35 | −5.20 | 8.91 |

4. Further ISE Models

To improve the initial results, two additional ISE models were constructed in order to achieve better results from scanning an external database. That was achieved with a different construction of the learning sets.

Model 1: "Best-Rest" Model.

The 53 inhibitors with top IC50 values of 3 to 250 nM were used as the set of actives, accompanied by 10,000 randomly picked molecules that were used as inactive or less actives. Filters with 5 descriptor ranges each were picked out of 114 different descriptors (table 6) and 5 final filters remained.

Those filters were used to distinguish between highly active ligands and random molecules.

TABLE 6

| Descriptor | "filtered" set | "full" set | "best rest" | "best worst" |
|---|---|---|---|---|
| a_acc | + | + | + | + |
| a_aro | + | + | + | + |
| a_base | + | | + | + |
| a_don | + | + | + | + |
| a_ICM | + | + | + | + |
| a_nBr | + | + | + | + |
| a_nCl | + | + | + | + |
| a_nF | + | + | + | + |
| a_nN | + | + | + | + |
| a_nO | + | + | + | + |
| a_nS | + | + | + | + |
| b_1rotR | + | + | + | + |
| b_double | + | + | + | + |
| b_triple | + | + | + | + |
| lip_acc | + | + | + | + |
| lip_don | + | + | + | + |
| lip_druglike | + | + | + | + |
| lip_violation | + | + | | |
| chilv_C | | + | + | + |
| BCUT_PEOE_1 | + | + | + | + |
| BCUT_PEOE_2 | + | + | + | + |
| BCUT_PEOE_3 | + | + | + | + |
| BCUT_SLOGP_0 | + | + | + | + |
| BCUT_SLOGP_1 | + | + | + | + |
| BCUT_SLOGP_2 | + | + | + | + |
| BCUT_SLOGP_3 | + | + | + | + |
| BCUT_SMR_1 | + | + | + | + |
| BCUT_SMR_2 | | + | + | + |
| GOUT_PEOE_0 | + | | | |
| GCUT_PEOE_1 | + | + | + | + |
| GCUT_PEOE_2 | + | + | + | + |
| GCUT_PEOE_3 | + | + | + | + |
| GCUT_SLOGP_1 | + | + | + | + |
| GCUT_SLOGP_2 | + | + | + | + |
| GCUT_SMR_1 | + | + | + | + |
| GCUT_SMR_2 | + | + | + | + |
| PEOE_VSA + 0 | + | + | + | + |
| PEOE_VSA + 1 | + | + | | |
| PEOE_VSA + 3 | + | + | + | + |
| PEOE_VSA + 4 | + | + | + | + |
| PEOE_VSA + 5 | + | + | + | + |
| PEOE_VSA + 6 | + | + | + | + |
| PEOE_VSA-0 | + | + | + | + |
| PEOE_VSA-1 | + | + | + | + |
| PEOE_VSA-2 | + | + | + | + |
| PEOE_VSA-3 | + | + | + | + |
| PEOE_VSA-4 | + | + | + | + |
| PEOE_VSA-5 | + | + | + | + |
| PEOE_VSA-6 | + | + | + | + |
| SlogP_VSA0 | + | + | + | + |
| SlogP_VSA1 | + | + | + | + |
| SlogP_VSA2 | + | + | + | + |
| SlogP_VSA3 | + | + | + | + |
| SlogP_VSA4 | + | + | + | + |
| SlogP_VSA5 | + | + | + | + |
| SlogP_VSA6 | + | + | + | + |
| SlogP_VSA7 | + | + | + | + |
| SlogP_VSA8 | + | + | + | + |
| SlogP_VSA9 | + | + | + | + |
| SMR_VSA0 | + | + | + | + |
| SMR_VSA1 | + | + | + | + |
| SMR_VSA2 | + | + | + | + |
| SMR_VSA3 | + | + | + | + |
| SMR_VSA4 | + | + | + | + |
| SMR_VSA5 | + | + | + | + |
| SMR_VSA7 | + | + | + | + |
| PEOE_PC− | + | + | + | + |
| PEOE_RPC+ | + | + | + | + |
| PEOE_RPC− | + | + | + | + |
| PEOE_VSA_FHYD | + | + | + | + |
| PEOE_VSA_NEG | + | + | + | + |
| PEOE_VSA_PPOS | + | + | + | + |
| Q_RPC− | + | + | + | + |
| Q_VSA_FHYD | + | + | + | + |
| Q_VSA_FPNEG | + | + | + | + |
| Q_VSA_FPPOS | + | + | + | + |
| Q_VSA_NEG | + | + | + | + |
| Q_VSA_POL | + | + | | |
| vsa_acc | + | + | + | + |
| vsa_base | + | + | + | + |
| vsa_don | + | + | + | + |
| vsa_other | + | + | + | + |
| balabanJ | + | + | + | + |
| chiral | + | + | | |
| chiral_u | + | + | + | + |
| logP(o/w) | + | + | + | + |
| logS | + | + | + | + |

TABLE 6-continued

| Descriptor | "filtered" set | "full" set | "best rest" | "best worst" |
|---|---|---|---|---|
| mutagenic | + | + | + | + |
| opr_brigid | + | + | + | + |
| opr_leadlike | + | + | + | + |
| opr_violation | + | + | + | + |
| petitjean | + | + | + | + |
| reactive | + | + | + | + |
| SlogP | + | + | + | + |
| TPSA | | + | + | + |
| vdw_area | + | + | + | + |
| a_acid | + | + | + | + |
| a_hyd | + | | | |
| b_1rotN | + | | | |
| GCUT_SLOGP_0 | + | | | |
| GOUT_SMR_0 | + | | | |
| PEOE_VSA + 2 | + | | + | + |
| SMR_VSA6 | + | | | |
| PEOE_PC+ | + | | | |
| PEOE_VSA_FNEG | + | + | + | + |
| PEOE_VSA_FPNEG | + | | + | + |
| PEOE_VSA_FPPOS | + | + | + | + |
| PEOE_VSA_PNEG | + | + | + | + |
| PEOE_VSA_POL | + | + | + | + |
| Q_RPC+ | + | + | + | + |
| Q_VSA_FNEG | + | | + | + |
| Q_VSA_HYD | + | | | |
| Q_VSA_PNEG | + | + | + | + |
| Q_VSA_PPOS | + | | + | + |
| vsa_pol | + | | + | + |
| density | + | + | + | + |
| FCharge | + | + | | |
| VAdjMa | + | + | + | + |
| VDistEq | + | | | |
| weinerPath | + | + | + | + |

Due to the small number of filters, the possible values of ISE indexes are limited: each model could produce only six values for the molecular ISE indexes, which are: −0.99, −0.59, −0.19, 0.19, 0.59 and 0.99. The models were tested on all the initial active and random molecules. The model gave only four FP above the ISE index of 0.0, and no FN below 0.0. MCC above the 0.5 index was 0.99.

Model 2: "Best-Worst" Model.

The model 2 was constructed from the same 53 highly active ligands as actives but the classification by ISE was limited to 236 molecules with weak activity above 3 µM as group of "inactive or less active" molecules.

In this model, there are no "assumed" inactives, as all activities of the learning set have been recorded earlier. Again, 114 descriptors were used for the model construction. 5 final filters retrieved. The model gave 3 FPs above 0, no FN below 0 and MCC for the 0.5 index of 0.98.

The 883 molecules which scored over 0.2 in the previous ISE model and filtered by applicability domain (FIG. 3) were scanned by both the "Best-Rest" and (subsequently) by the "Best-Worst" models. Solubility was evaluated as before. Eventually, 30 molecules were selected for vitro tests (table 7). Said molecules were purchased at the Enamine online store (https://www.enaminestore.com/catalog).

TABLE 7

| Enamine name | ISE initial | "Best Worst" ISE index | "Best Rest" ISE index | logS MOE | logS Enamine | logS VCCLAB | logS admetSAR | IC50 in [µM] |
|---|---|---|---|---|---|---|---|---|
| Best results of both models |||||||||
| T5453081 (7) | 0.246 | 0.992 | 0.995 | −4.63604 | −4.621 | −5.69 | −2.4459 | 1.6 |
| T5669070 (1) | 0.379 | 0.992 | 0.995 | −5.60773 | −3.723 | −6.35 | −2.6583 | 0.0536 |
| T5985177 | 0.32 | 0.596 | 0.995 | −4.34383 | −3.019 | −5.35 | −2.2473 | 148.87 |
| T5635793 (14) | 0.311 | 0.596 | 0.597 | −4.90188 | −3.964 | −8.36 | −2.4118 | 6.32 |
| T6216617 (18) | 0.229 | 0.595 | 0.995 | −4.24242 | −2.474 | −7.07 | −1.7063 | 7.56 |
| T6083277 (17) | 0.236 | 0.595 | 0.995 | −5.65728 | −3.484 | −7.38 | −2.2276 | 7.51 |
| T5581953 (2) | 0.294 | 0.595 | 0.995 | −3.97495 | −3.663 | −6.32 | −2.8638 | 0.201 |
| T5581957 | 0.228 | 0.595 | 0.597 | −4.06466 | −3.16 | −6.33 | −2.6293 | 30.1 |
| T5581955 (6) | 0.233 | 0.595 | 0.597 | −4.65277 | −4.328 | −6.57 | −2.9648 | 1.44 |
| T5587050 (10) | 0.233 | 0.595 | 0.597 | −4.85454 | −4.76 | −6.76 | −3.0466 | 1.87 |
| T5570245 (3) | 0.341 | 0.595 | 0.597 | −5.43096 | −4.005 | −4.96 | −2.6715 | 0.815 |
| Best results of "Best Worst" |||||||||
| T5364934 (8) | 0.253 | 0.992 | −0.597 | −4.43656 | −5.009 | −5.62 | −2.3575 | 1.62 |
| T6024046 | 0.24 | 0.596 | −0.995 | −4.17173 | −1.743 | −5.23 | −2.8245 | 212.12 |
| T5820428 (9) | 0.262 | 0.596 | −0.995 | −3.99165 | −3.509 | −5.86 | −2.9813 | 1.78 |
| T6683896 (4) | 0.263 | 0.596 | −0.995 | −4.35115 | −4.645 | −6.35 | −3.1675 | 0.896 |
| T5827068 | 0.319 | 0.596 | −0.995 | −4.28382 | −3.008 | −8.49 | −2.2608 | 16.43 |
| T5980807 | 0.328 | 0.596 | −0.995 | −4.26701 | −2.664 | −5.35 | −2.1885 | 208.7 |
| T5571341 (11) | 0.234 | 0.595 | −0.597 | −5.6069 | −4.93 | −7.32 | −2.1763 | 3.14 |
| T5793071 (15) | 0.268 | 0.595 | −0.597 | −4.69138 | −3.872 | −8.37 | −2.5675 | 6.43 |
| T5772889 | 0.351 | 0.595 | −0.597 | −4.17271 | −3.146 | −8.05 | −2.3403 | 66.82 |
| T5771901 | 0.352 | 0.595 | −0.597 | −3.97094 | −2.883 | −7.79 | −2.4109 | 13.27 |
| T5489244 | 0.221 | 0.595 | −0.995 | −4.09807 | −3.362 | −7.47 | −2.5198 | 25.52 |
| T5581956 (12) | 0.294 | 0.595 | −0.995 | −4.32556 | −4.215 | −6.51 | −2.7295 | 3.16 |
| Best results of "Best Rest" |||||||||
| T5642393 | 0.294 | 0.199 | 0.995 | −4.07038 | −4.311 | −6.38 | −2.2189 | 33.8 |
| T5570252 | 0.295 | 0.199 | 0.995 | −3.96087 | −3.56 | −6.26 | −1.8119 | 13.2 |
| T0503-2983 (16) | 0.245 | 0.199 | 0.597 | −4.5931 | −3.696 | −5.56 | −2.9722 | 6.78 |
| T5610833 | 0.245 | 0.198 | 0.597 | −6.16553 | −5.495 | −5.25 | −3.0482 | 29.62 |
| T5594499 | 0.306 | 0.198 | 0.597 | −5.69161 | −5.113 | −5.27 | −2.8718 | 274.54 |
| T5428933 (5) | 0.229 | −0.198 | 0.995 | −4.28311 | −3.232 | −9.22 | −2.9516 | 0.962 |
| T5535483 (13) | 0.234 | −0.595 | 0.995 | −4.90758 | −3.451 | −7.32 | −3.0167 | 3.82 |

Table 7 indicates for the various Enamines analysed (compound numbering in brackets) the results of the in vitro tests.

Inhibition was tested in the presence of 5 µM of the ODN 2216 agonist.

All 30 compounds showed inhibitory activity, the worst IC50 is 274 µM and the average IC50 value is 37.6 µM (without the 4 worst values the average becomes 11 µM).

17 out of the 30 compounds showed high inhibitory levels (under 10 µM). The IC50 values of 11 best rated molecules by both of the optimization models are in the range of 0.053-148.87 µM; with an average IC50 value of 18.7 µM (without the worst value the average becomes 5.7 µM).

The IC50 values of 7 best rated molecules by "Best Rest" optimization model are in a range of 0.962-274.54 µM; with an average IC50 value of 51.8 µM (without the worst value the average becomes 14.7 µM).

The IC50 values of 12 best rated compounds by "Best Worst" optimization models are in a range of 0.896-212.12 µM; with average IC50 value of 46.7 µM (without the 2 worst value the average becomes 13.9 µM).

Five molecules showed nano-molar value, with the best compound with IC50 of 53.6 nM shown at table 7.

5. Summary

The virtual screening was employed on a large virtual Enamine database of 1.8 million molecules. Only 1789 molecules ('0.1% of the total) passed our ISE initial model above an index value of 0.2, and 229 passed the 0.4 index. This reflects a very high specificity of the model, as may be seen by the evaluation by MCC (0.313) score and by its enrichment factor of 35.7. After applicability and solubility filtering, out of 229 candidates, 30 were chosen for in vitro tests and out of those 26 active antagonists were discovered, when 9 out of them were antagonists with relatively low µM values (under 16 µM). Those results imply the high distinguishing features of the chosen ISE model, while the range of activity values retrieved (µM-mM) ideally satisfies the initial aim, which is distinguishing between inactive or less actives and molecules with activity for the TLR9.

As could be seen from the physico-chemical molecular descriptors that constructed those filters, most of the unique parameters of the actives are complicatedly calculated features which include parameters like surface area, partial calculated charges, calculation matrixes and their contribution to other parameters. Thus, it can be deduced that there is no simple unique feature attributed for TLR9 known antagonist ligands. However, comparing with the initial model, the optimization model retrieved very highly active compounds, while most of them showed very low IC50 values. Moreover, all of the best rated compounds by those models were active.

From the 883 molecules that conformed to the applicability domain and were indexed above 0.2 by the initial ISE, 30 final candidates for in vitro tests were selected. These candidates were predicted as actives by one of the optimization models or by both of them. For comparison and evaluation of the optimization models separately, the molecules were selected in a way that 11 of them showed highest results in both of the models, 7 showed high results only for "Best Worst" model and 12 showed high results only for "Best Rest" model.

The in vitro tests showed very good results for all of the molecules for both of the optimization models separately, as well as for the combination of the models. The average activity value for the 11 best rated compounds by both of the models is 18.7 µM, and 5.7 µM excluding the worst compound (148.87 µM).

The average activity value for all 18 compounds (table 7; molecules listed in "Best results of both models" and "Best results of "Best Rest") of the "Best Rest" model is 33.42 µM, and for all the 23 best rated compounds of "Best Worst" model is 33.31 µM.

Excluding four worst molecules the average activity values are 9.66 µM and 9.82 µM, respectively. Five compounds under 1 µM were retrieved, when each of the models retrieved four of them, so that three out of these five highly active compounds were recognized by both models.

Those results imply that both of the models distinguish correctly and very specifically between the dominant features of highly active compounds and between irrelevant features of foreign molecules, while each model separately concentrates on a little bit different set of features. Due to this fact, one model can filter out active molecules which were selected by the other model. As a conclusion, for optimization of discovering highly active molecules, the usage of both models is advantageous.

Tanimoto similarity ($T_c$ values) between molecules in a set reflects the diversity and the uniqueness of a method of discovery. Out of 60 compound 10 (17%) have a similarity lower than $T_c$=0.5 comparing with all the other molecules, thus considered as different scaffolds. When 45 molecules (75%) have maximum similarity values lower than $T_c$=0.85 thus considered not to be very similar to other molecules. The average of similarities of these molecules is very low, $T_c$=0.28.

A major similarity issue is always, whether the discovered molecules are similar or not to the model from which they were derived. With ISE (Glick, M.; Rayan, A.; Goldblum, A., A stochastic algorithm for global optimization and for best populations: a test case of side chains in proteins. Proc. Natl. Acad. Sci. USA 2002, 99 (2), 703-8), this is not the case. The similarity of the 60 discovered compounds to the known TLR9 antagonists that were used for model construction was examined in more detail.

Comparison of the resulted 60 inventive molecules (abbreviated as "IM" in table 8) with CHEMBL TLR9 actives (abbreviated as "CM" in table 8) shows that 43 of them (71%) have a maximum similarity to CHEMBL compounds below 0.5 and 56 out of those 60 (93%) have a maximum similarity below 0.7. It can thus be deduced that most of the newly discovered compounds are different than the known CHEMBL compounds (table 8).

TABLE 8

| average similarity | | maximum similarity | | Enamine |
|---|---|---|---|---|
| CM | IM | CM | IM | name |
| 0.17 | 0.31 | 0.41 | 0.82 | T5642393 |
| 0.19 | 0.27 | 0.37 | 1.00 | T5666774 |
| 0.21 | 0.31 | 0.71 | 0.67 | T5669070 |

TABLE 8-continued

| average similarity | | maximum similarity | | Enamine name |
|---|---|---|---|---|
| CM | IM | CM | IM | |
| 0.20 | 0.30 | 0.73 | 0.88 | T5702130 |
| 0.20 | 0.29 | 0.64 | 0.81 | T5713724 |
| 0.18 | 0.26 | 0.54 | 0.73 | T5762626 |
| 0.20 | 0.32 | 0.57 | 0.56 | T5771455 |
| 0.16 | 0.26 | 0.36 | 0.80 | T5771901 |
| 0.17 | 0.28 | 0.34 | 0.54 | T5771936 |
| 0.15 | 0.24 | 0.38 | 0.87 | T5771955 |
| 0.16 | 0.26 | 0.36 | 0.69 | T5772889 |
| 0.16 | 0.24 | 0.40 | 0.80 | T5793071 |
| 0.20 | 0.30 | 0.50 | 0.65 | T5803292 |
| 0.18 | 0.24 | 0.67 | 0.81 | T5807811 |
| 0.20 | 0.30 | 0.44 | 0.77 | T5820428 |
| 0.18 | 0.28 | 0.37 | 0.66 | T5827068 |
| 0.17 | 0.24 | 0.64 | 0.81 | T5922759 |
| 0.16 | 0.26 | 0.29 | 0.85 | T5980807 |
| 0.16 | 0.25 | 0.28 | 0.85 | T5985177 |
| 0.21 | 0.29 | 0.45 | 0.45 | T6015017 |
| 0.15 | 0.24 | 0.30 | 0.79 | T6024046 |
| 0.18 | 0.34 | 0.41 | 0.93 | T6083277 |
| 0.18 | 0.31 | 0.49 | 0.75 | T6216617 |
| 0.19 | 0.27 | 0.52 | 0.73 | T6306924 |
| 0.17 | 0.27 | 0.34 | 0.54 | T6416309 |
| 0.17 | 0.24 | 0.43 | 0.78 | T6495030 |
| 0.21 | 0.28 | 0.58 | 0.77 | T6549007 |
| 0.17 | 0.25 | 0.36 | 0.69 | T6593995 |
| 0.19 | 0.26 | 0.39 | 0.77 | T6683896 |
| 0.20 | 0.31 | 0.79 | 0.88 | T6895608 |
| 0.19 | 0.28 | 0.42 | 0.78 | T0501-0693 |
| 0.19 | 0.29 | 0.48 | 0.78 | T0501-1111 |
| 0.16 | 0.19 | 0.30 | 0.24 | T0502-6934 |
| 0.19 | 0.31 | 0.36 | 0.48 | T0503-2983 |
| 0.15 | 0.24 | 0.40 | 0.47 | T0504-1221 |
| 0.18 | 0.24 | 0.93 | 0.55 | T0504-1257 |
| 0.17 | 0.18 | 0.39 | 0.34 | T0505-2171 |
| 0.20 | 0.26 | 0.54 | 0.77 | T0506-4124 |
| 0.15 | 0.25 | 0.38 | 0.87 | T0513-2251 |
| 0.20 | 0.30 | 0.49 | 0.48 | T0513-5752 |
| 0.19 | 0.27 | 0.37 | 1.00 | T0519-4581 |
| 0.16 | 0.24 | 0.27 | 0.45 | T5364934 |
| 0.16 | 0.28 | 0.30 | 0.45 | T5428933 |
| 0.18 | 0.27 | 0.53 | 0.56 | T5453081 |
| 0.19 | 0.26 | 0.43 | 0.46 | T5456813 |
| 0.18 | 0.25 | 0.35 | 0.48 | T5489244 |
| 0.19 | 0.28 | 0.54 | 0.68 | T5500062 |
| 0.17 | 0.29 | 0.42 | 0.82 | T5535483 |
| 0.18 | 0.29 | 0.40 | 0.78 | T5547436 |
| 0.17 | 0.28 | 0.34 | 0.65 | T5570245 |
| 0.17 | 0.30 | 0.43 | 0.77 | T5570252 |
| 0.18 | 0.34 | 0.41 | 0.93 | T5571341 |
| 0.18 | 0.34 | 0.39 | 0.96 | T5581953 |
| 0.18 | 0.33 | 0.39 | 0.99 | T5581955 |
| 0.18 | 0.34 | 0.39 | 0.92 | T5581956 |
| 0.17 | 0.34 | 0.37 | 0.90 | T5581957 |
| 0.18 | 0.33 | 0.38 | 0.99 | T5587050 |
| 0.21 | 0.34 | 0.66 | 0.98 | T5594499 |
| 0.21 | 0.34 | 0.65 | 0.98 | T5610833 |
| 0.19 | 0.31 | 0.41 | 0.66 | T5635793 |
| 0.18 | 0.28 | 0.45 | 0.45 | AVERAGE |
| 0.21 | 0.34 | 0.93 | 0.93 | MAXIMUM |

The Tanimoto similarity within the previously known CHEMBL TLR9 antagonists is different: Out of 230 compounds only 61 (26%) have a Tanimoto similarity lower the 0.5 and may be considered different scaffolds, while 104 (45%) have Tanimoto index lower than 0.85. Thus, although started with a set of TLR9 antagonists that share molecular features, TLR9 antagonists were obtained that does not share such features. These results represent the ability to discover new compounds with new scaffolds, even though using for model construction compounds with relatively low diversity. The diversity of the discovery set is much greater than the diversity of the modeling set.

What is claimed is:

1. A method of treating a toll-like receptor 9-mediated disease characterized by an excessive immune response in a subject in need thereof, the method comprising:

administering to the subject a composition comprising an active component, wherein the active component is a first compound, a second compound, a third compound, a pharmaceutically acceptable salt thereof, a solvate thereof, or a combination thereof, and wherein:

the first compound is selected from a first group consisting of:

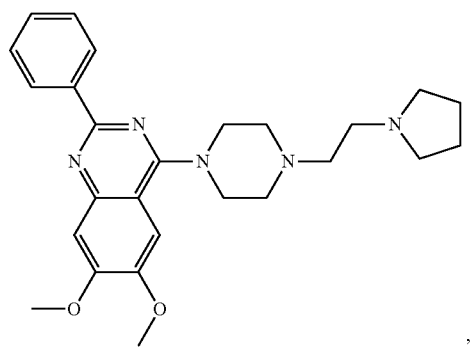

1

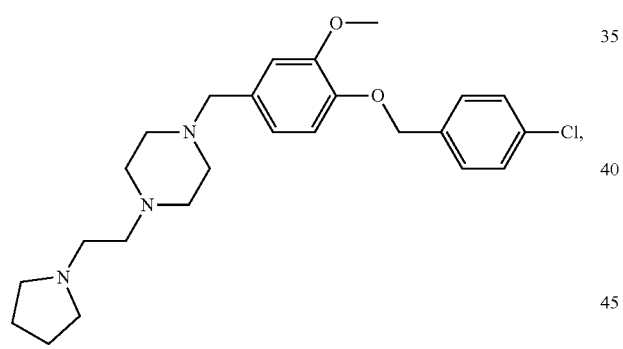

5

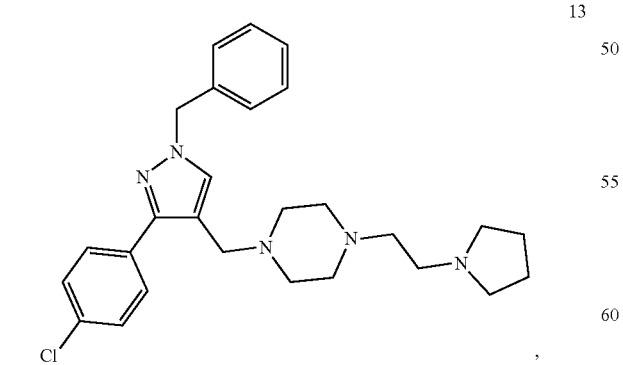

13 and combinations thereof, the second compound is selected from a second group consisting of:

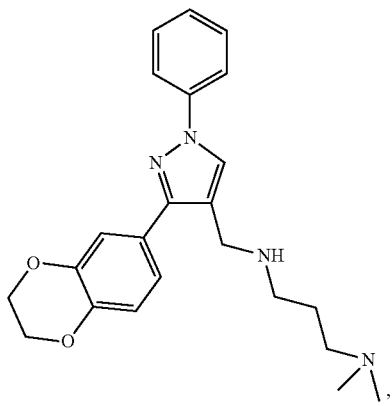

2

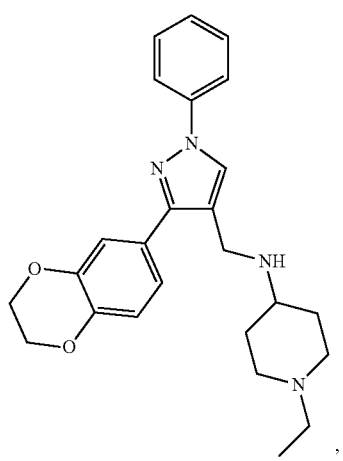

6

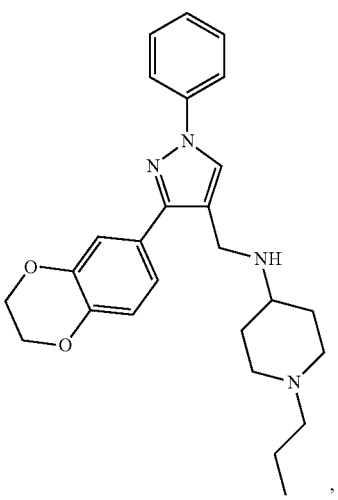

10

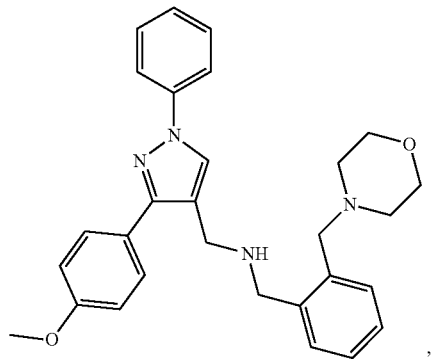

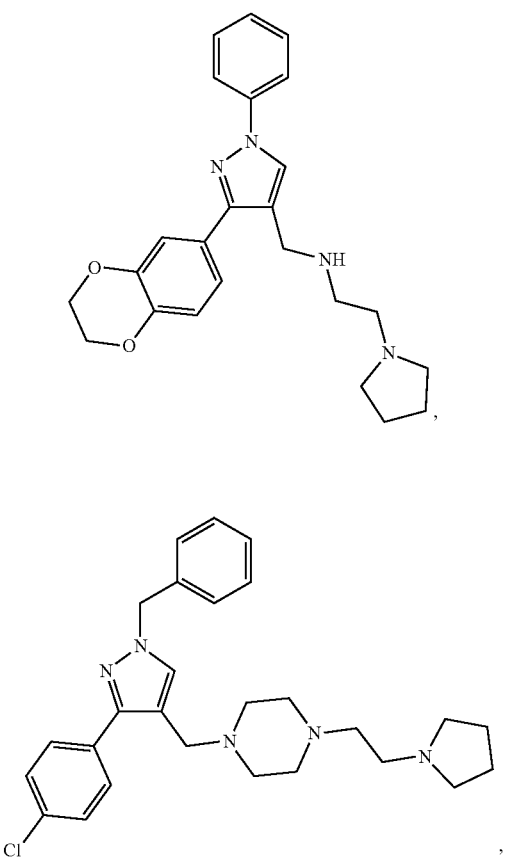

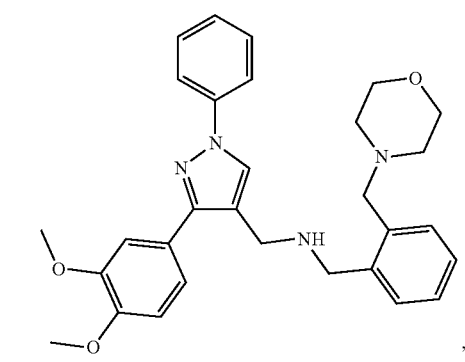

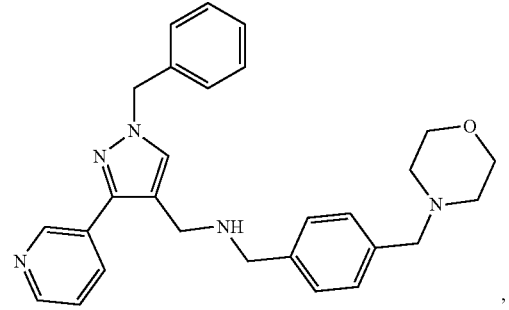

and combinations thereof, and
the third compound is selected from a third group consisting of:

and combinations thereof.

2. The method according to claim 1, comprising administering to the subject a composition comprising at least the first compound, a pharmaceutically acceptable salt thereof, or a solvate thereof.

3. The method according to claim 1, comprising administering to the subject a composition comprising at least the second compound, a pharmaceutically acceptable salt thereof, or a solvate thereof.

4. The method according to claim 1, comprising administering to the subject a composition comprising at least the third compound, a pharmaceutically acceptable salt thereof, or a solvate thereof.

5. The method according to claim 1, wherein the disease is a toll-like receptor 9 (TLR9)-mediated autoimmune disease, an atopic disease, a transplant rejection, or sepsis.

6. The method according to claim 1, wherein the disease is lupus erythematosus, multiple sclerosis, rheumatoid arthritis, atopic dermatitis, hyperlipidaemia, atheroxclerosis, or sepsis.

7. The method according to claim 1, wherein the subject is human or a non-human mammal.

8. A method of treating a toll-like receptor 9-mediated disease characterized by an excessive immune response in a subject in need thereof, the method comprising:
administering to the subject a composition comprising an active component,
wherein the active component is selected from the group consisting of:

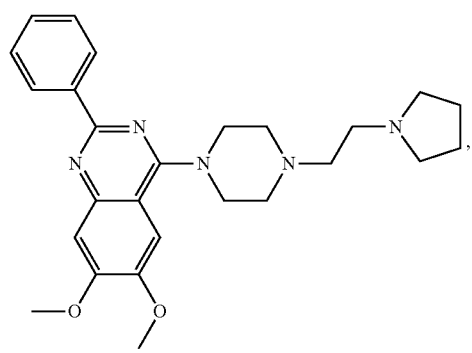
1

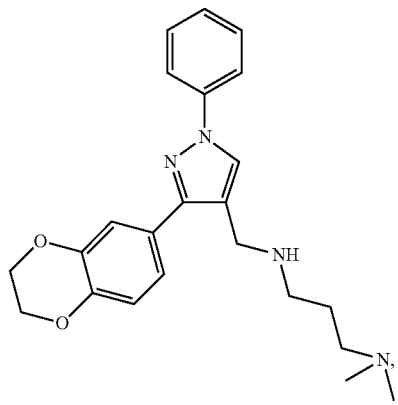
2

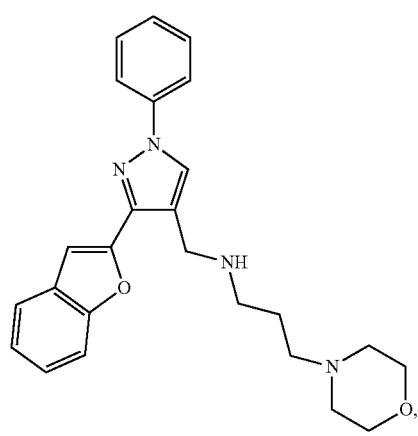
3

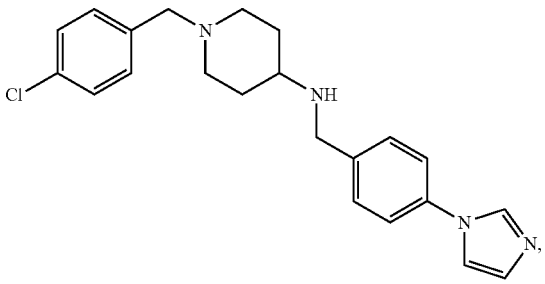
4

-continued

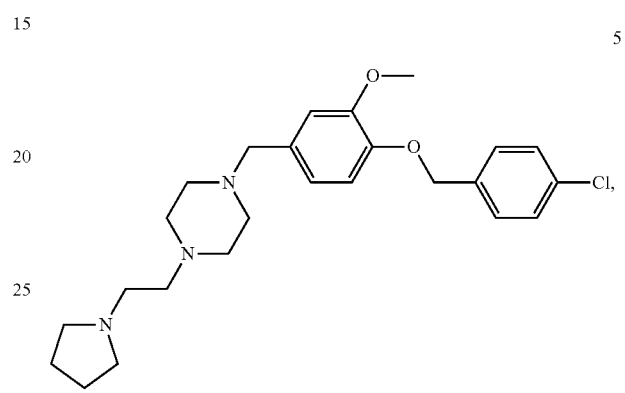
5, 6, 7, 8

9
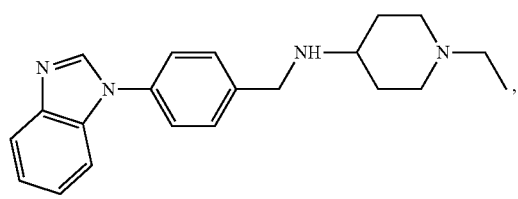
10
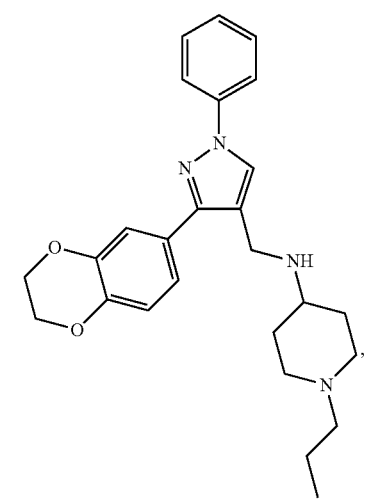
11
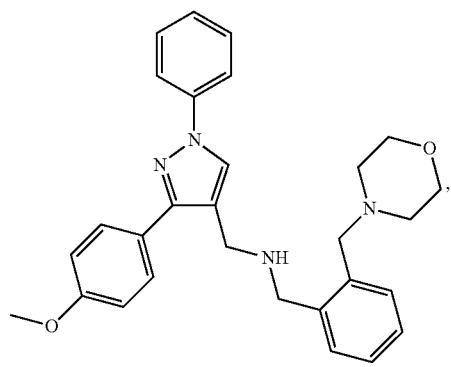
12
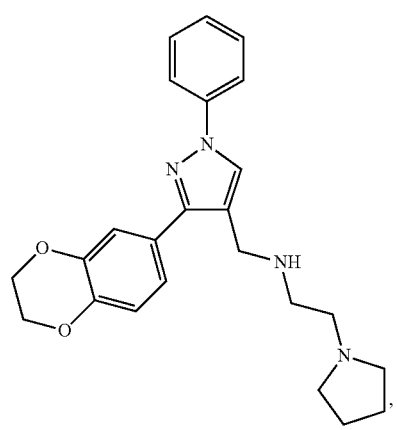
13
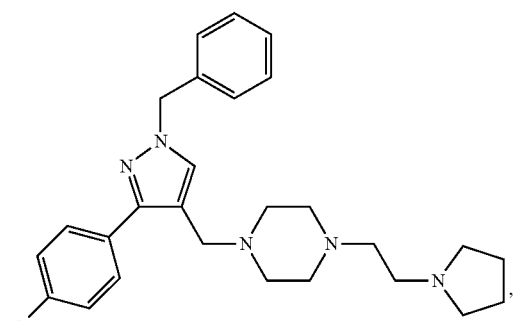
14
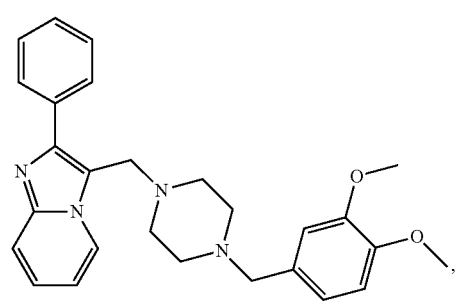
15
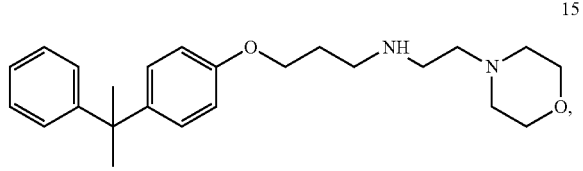
16
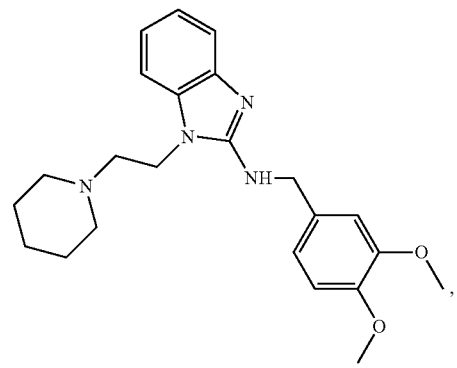
17
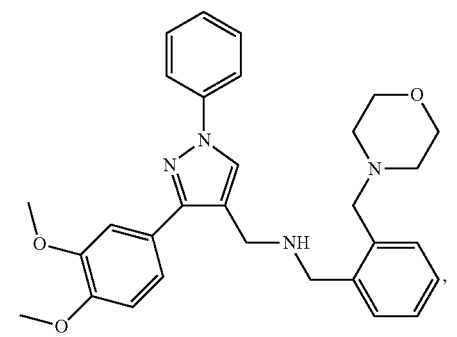

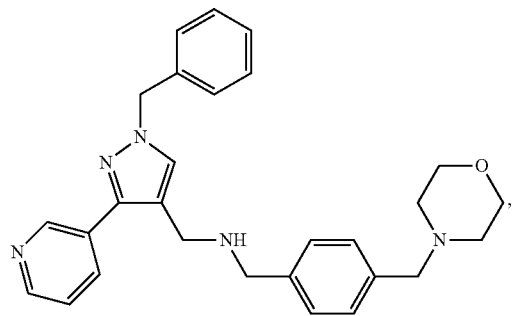
18
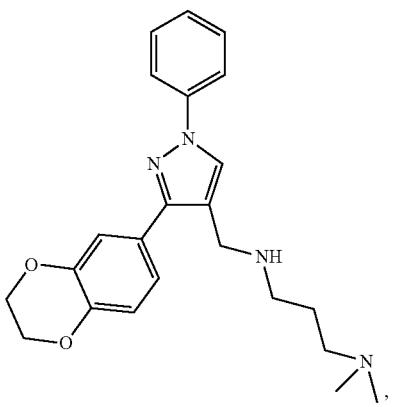
2
pharmaceutically acceptable salts thereof, solvates thereof, and combinations thereof.
9. The method according to claim 8, wherein the active component is selected from the group consisting of:
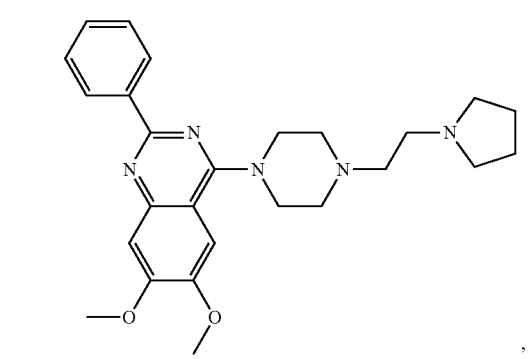
1
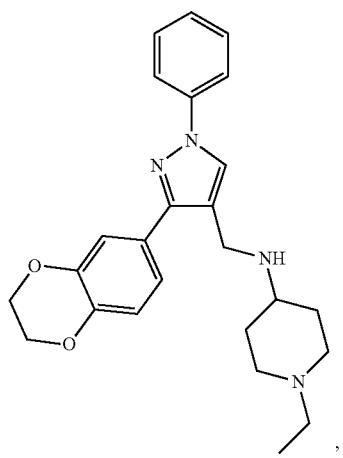
6
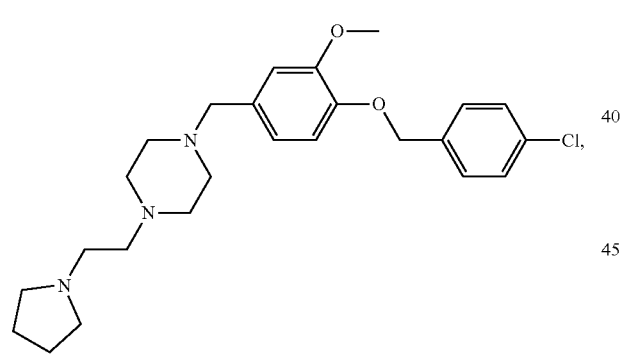
5
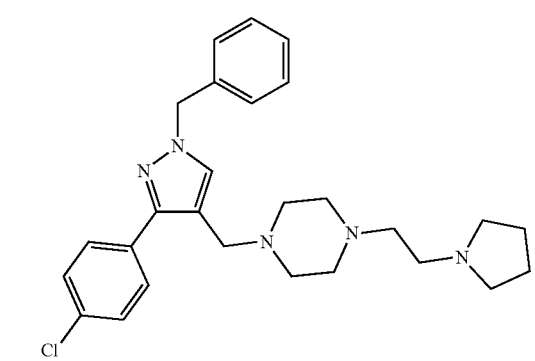
13
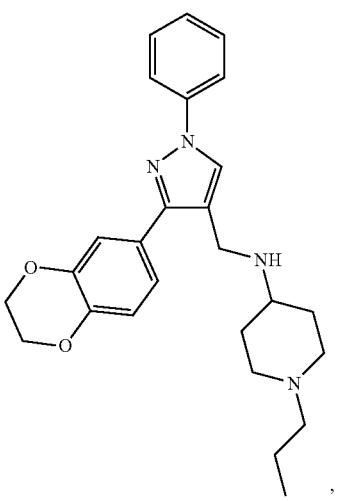
10
and a combination thereof.
10. The method according to claim 8, wherein the active component is selected from the group consisting of:

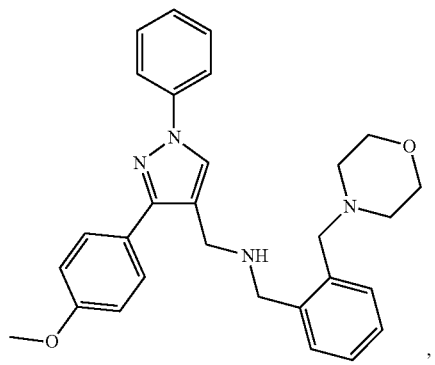

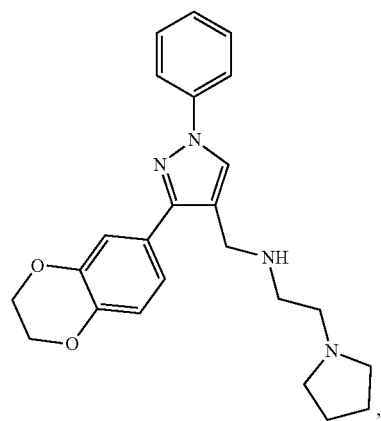

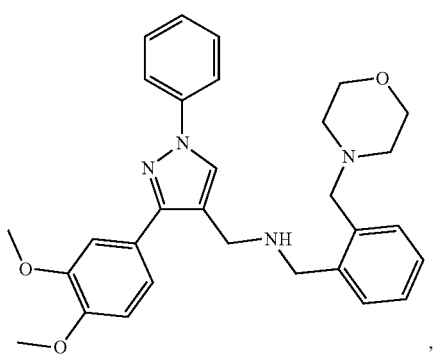

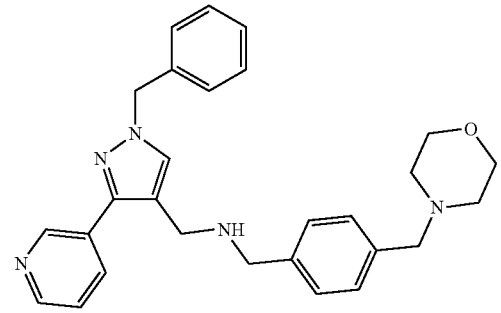

and a combination thereof.

11. The method according to claim 8, wherein the active component is selected from the group consisting of:

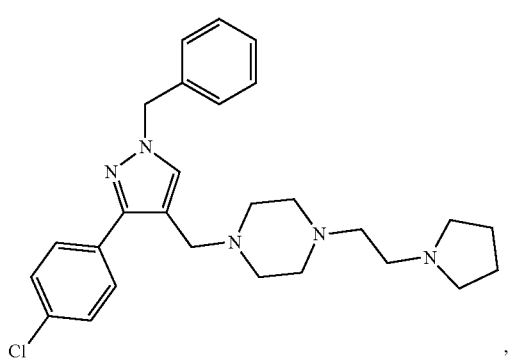

and a combination thereof.

12. The method according to claim 8, wherein the disease is a toll-like receptor 9 (TLR9)-mediated autoimmune disease, an atopic disease, a transplant rejection, or sepsis.

13. The method according to claim 8, wherein the disease is lupus erythematosus, multiple sclerosis, rheumatoid arthritis, atopic dermatitis, hyperlipidaemia, atheroxclerosis, or sepsis.

14. The method according to claim 8, wherein the subject is human or a non-human mammal.

15. The method according to claim 8, wherein the composition further comprises a pharmaceutically acceptable carrier.

16. The method according to claim 8, further comprising:
administering to the subject at least one of a toll like receptor 3 (TLR3) antagonist, a toll like receptor 7 (TLR7) antagonist, or a toll like receptor 8 (TLR38) antagonist.

* * * * *